US012611424B2

(12) United States Patent
Barritault

(10) Patent No.: US 12,611,424 B2
(45) Date of Patent: Apr. 28, 2026

(54) COSMETIC/DERMATOLOGICAL COMPOSITION

(71) Applicants: Organes, Tissus Régénération, Réparation, Remplacement, Paris (FR); Denis Barritault, Paris (FR)

(72) Inventor: Denis Barritault, Paris (FR)

(73) Assignees: Denis Barritault, Paris (FR); Organes, Tissus: Régénération, Réparation, Remplacement, Paris (FR)

( * ) Notice: Subject to any disclaimer, the term of this patent is extended or adjusted under 35 U.S.C. 154(b) by 32 days.

(21) Appl. No.: 17/425,244

(22) PCT Filed: Dec. 30, 2019

(86) PCT No.: PCT/EP2019/087146
§ 371 (c)(1),
(2) Date: Jul. 22, 2021

(87) PCT Pub. No.: WO2020/151900
PCT Pub. Date: Jul. 30, 2020

(65) Prior Publication Data

US 2022/0088061 A1 Mar. 24, 2022

(30) Foreign Application Priority Data

Jan. 24, 2019 (EP) .................................... 19305095

(51) Int. Cl.
*A61K 31/765* (2006.01)
*A61K 8/86* (2006.01)
*A61Q 19/00* (2006.01)

(52) U.S. Cl.
CPC .............. *A61K 31/765* (2013.01); *A61K 8/86* (2013.01); *A61Q 19/007* (2013.01)

(58) Field of Classification Search
CPC ........ A61K 8/86; A61K 8/735; A61K 31/728; A61K 31/737; A61K 31/765;
(Continued)

(56) References Cited

U.S. PATENT DOCUMENTS 6,689,741 B2 2/2004 Barritault et al.
7,998,922 B2 * 8/2011 Barritault ................ A61P 17/16 514/1

(Continued)

FOREIGN PATENT DOCUMENTS

EP 1677807 A2 7/2006
EP 2260853 A2 12/2010

(Continued)

OTHER PUBLICATIONS

International Search Report issued by the International Search Authority corresponding to PCT/EP2019/087146, dated Jul. 30, 2020.

(Continued)

*Primary Examiner* — Hong Yu
(74) *Attorney, Agent, or Firm* — ArentFox Schiff LLP

(57) ABSTRACT

The present invention relates to a pharmaceutical or dermatological composition and to its use as a medicament. The present invention also relates to a cosmetic or dermatological composition, as well as to a care kit including the composition of the invention. The present invention finds an application in particular in the cosmetic, pharmaceutical and veterinary fields.

13 Claims, 1 Drawing Sheet

| Famille de produits RGTA OTR412 | Famille de produit OTR413 |
| --- | --- |
|  |  |

(58) Field of Classification Search
CPC ...... A61K 2300/00; A61P 11/00; A61P 17/00; A61P 17/02; A61P 19/02; A61P 25/28; A61P 27/02; A61Q 19/007; A61Q 19/08
See application file for complete search history.

(56) References Cited

U.S. PATENT DOCUMENTS

| | | | | |
|---|---|---|---|---|
| 8,476,220 | B2 * | 7/2013 | Barritault ................ | A61P 39/00 514/59 |
| 8,790,631 | B2 * | 7/2014 | Barritault ................ | A61P 29/00 424/78.17 |
| 8,883,715 | B2 * | 11/2014 | Barritault ................ | A61P 17/00 435/375 |
| 11,351,190 | B2 * | 6/2022 | Barritault ............. | A61K 9/0053 |
| 2007/0141020 | A1 | 6/2007 | Barritault et al. | |
| 2009/0092591 | A1 * | 4/2009 | Diehl .............. | C12Y 111/01006 424/94.2 |
| 2010/0074851 | A1 * | 3/2010 | Dubois .................. | A61K 8/416 424/59 |
| 2014/0301972 | A1 | 10/2014 | Barritault et al. | |
| 2018/0125880 | A1 | 5/2018 | Barritault | |
| 2023/0113110 | A1 * | 4/2023 | Barritault ............. | A61K 31/728 424/78.27 |

FOREIGN PATENT DOCUMENTS

| | | | |
|---|---|---|---|
| EP | 12305414 | | 4/2012 |
| EP | 3000475 | A1 | 3/2016 |
| EP | 3097922 | A1 | 11/2016 |
| FR | 2861308 | A1 | 4/2005 |
| JP | 2002521503 | A | 7/2002 |
| WO | WO 2016/189088 | A1 * | 12/2016 |

OTHER PUBLICATIONS

Barritault, Denis, et al., "RGTA or ReGenerating Agents Mimic Heparan Sulfate in Regenerative Medicine: from concept to curing patients", Glycoconjugate Journal, Dec. 7, 2016, pp. 325-338, vol. 34, No. 3, Boston.

Anonymous, "OTR3 Organ, Tissue, Regeneration, Repair, Replacement", Website, Retrieved Jan. 1, 2017, www.pharmetikon.com/wp-content/uploads/2017/02/Presentation-CACIPLIQ-04.2016_v-distributeurs.pdf.

Tiwari, Sanjay, et al., "Modified Hyaluronic Acid Based Materials for Biomedical Applications", International Journal of Biological Marcomolecules, Oct. 12, 2018, pp. 556-571, vol. 121.

Voigt, J. et al., Hyaluronic acid derivatives and their healing effect on burns, epithelial surgical wounds, and chronic wounds: A systematic review and meta-analysis of randomized controlled trials. Wound Repair and Regeneration, May 4, 2012, vol. 20, No. 3, pp. 317-331.

Tiwari et al., "Modified hyaluronic acid based materials for biomedical applications", Int J Biol Macromol. Jan. 2018;121:556-571.

Bukhari et al., "Hyaluronic acid, a promising skin rejuvenating biomedicine: A review of recent updates and pre-clinical and clinical investigations on cosmetic and nutricosmetic effects", Int J Biol Macromol. Dec. 2018;120(Pt B):1682-1695.

Diamond, "Reduction of postoperative adhesion development", Fertil Steril. Oct. 2016;106(5):994-997.e1.

Alexakis et al., "Reversal of abnormal collagen production in Crohn's disease intestinal biopsies treated with regenerating agents", Gut. Jan. 2004;53(1):85-90.

Yue et al., "Insights on a new path of pre-mitochondrial apoptosis regulation by a glycosaminoglycan mimetic", Cell Death and Differ. May 2009;16(5):770-81.

Mangoni et al., "Differential effect triggered by a heparan mimetic of the RGTA family preventing oral mucositis without tumor protection", Int J Radiat Oncol Biol Phys. Jul. 15, 2009;74(4):1242-50.

Garcia-Filipe, et al., "RGTA OTR4120, a heparan sulfate mimetic, is a possible long-term active agent to heal burned skin", J Biomed Mater Res A. Jan. 2007;80A(1):75-8; first published online: Sep. 6, 2006.

Rouet et al., "Heparin-like synthetic polymers, named RGTAs, mimic biological effects of heparin in vitro", J Biomed Mater Res A. Sep. 15, 2006;78(4):792-7.

Meddahi et al., "FGF protection and inhibition of human neutrophil elastase by carboxymethyl benzylamide sulfonate dextran derivatives", Int J Biol Macromol. Feb. 1996;18(1-2):141-5.

Ledoux et al., "Human plasmin enzymatic activity is inhibited by chemically modified dextrans", J Biol Chem. Sep. 22, 2000, 275(38):29383-90.

Zimowska et al., "Heparan sulfate mimetics modulate calpain activity during rat Soleus muscle regeneration", J Cell Physiol. Aug. 2001;188(2):178-87.

Barritault et al., "RGTA® or ReGeneraTing Agents mimic heparan sulfate in regenerative medicine: from concept to curing patients", Glycoconj J. Jun. 2017;34(3):325-338.

Tammi et al., "Hyaluronan metabolism in skin", Progress in Histochemistry & Cytochemistry. 1994;29(2):1-81.

Stern et al., "Hyaluronan fragments: An information-rich system", European Journal of Cell Biology. 2006;699-715.

Ikeda et al., "Synthesis and biological activities of a library of glycosaminoglycans mimetic oligosaccharides", Biomaterials. 2011;32:769-776.

Barritault et al., "RGTA®-based matrix therapy—A new branch of regenerative medicine in locomotion", Joint Bone Spine. May 2016;84(3):283-292.

Frescaline et al., "Glycosaminoglycan Mimetic Associated to Human Mesenchymal Stem Cell-Based Scaffolds Inhibit Ectopic Bone Formation, but Induce Angiogenesis In Vivo", Tissue Eng Part A. Jul. 2013;19(13-14):1641-53.

Jacquet-Guibon et al., "Randomized controlled trial demonstrates the benefit of RGTA® based matrix therapy to treat tendinopathies in racing horses", PLoS One. Mar. 9, 2018;13(3):1-16.

Holmes et al., "Heparan sulfate proteoglycans mediate internalization and propagation of specific proteopathic seeds", Proc Natl Acad Sci. Aug. 13, 2013;110(33):E3138-47.

Ouidja et al., "Structure-activity studies of heparan mimetic polyanions for anti-prion therapies", Biochem Biophys Res Commun. Nov. 9, 2007;363(1):95-100.

Zerbinati et al., "In Vitro Evaluation of the Sensitivity of a Hyaluronic Acid PEG Cross-Linked to Bovine Testes Hyaluronidase", Open Access Maced J Med Sci. Jan. 25, 2018; 6(1):20-24.

Sall et al., "Comparison of the sensitivity of 11 crosslinked hyaluronic acid gels to bovine testis hyaluronidase", PolymDegrad Stab. 2007; 92: 915-919.

Reissig et al., "A modified colorimetric method for the estimation of N-acetylamino sugars", J Biol Chem. 1955;217:959e96.

Desgranges et al., "A substituted dextran enhances muscle fiber survival and regeneration in ischemic and denervated rat EDL muscle", J. Faseb J. Apr. 1999;13(6):761-6.

Yamauchi et al., "New agents for the treatment of infarcted myocardium", Faseb J. Nov. 2000;14(14):2133-4.

Asselot-Chapel et al., "Expression of fibronectin and interstitial collagen genes in smooth muscle cells: modulation by low molecular weight heparin fragments and serum", Biochem Pharmacol. Mar. 1, 1995;49(5):653-9.

Fajnkuchen et al., "Evaluation of a new matrix regenerating agent in patients with Sjögren syndrome and superficial ulcerative keratitis resistant to conventional therapy: A report of 3 cases", Medicine (Baltimore). Mar. 2018;97(10):e9935.

Malaq et al., "A Rapid Response to Matrix Therapy With RGTA in Severe Epidermolysis Bullosa", Eplasty; 12:ic15. Epub Oct. 17, 2012.

Khelif et al., "A heparan sulfate-based matrix therapy reduces brain damage and enhances functional recovery following stroke", Theranostics. Nov. 12, 2018;8(21):5814-5827.

Highley et al., "Jammed Microgel Inks for 3D Printing Applications", Adv Sci (Weinh). 2019;6(1):1801076.

(56) References Cited

OTHER PUBLICATIONS

Chen et al., "Collagen/heparin sulfate scaffolds fabricated by a 3D bioprinter improved mechanical properties and neurological function after spinal cord injury in rats", J Biomed Mater Res A. May 2017;105(5):1324-1332.
Lee et al., "Development and Evaluation of Hyaluronic Acid-Based Hybrid Bio-Ink for Tissue Regeneration", Tissue Eng Regen Med. Sep. 21, 2018;15(6):761-769.
Carnicer, "Preliminary report—ultrasonographic evolution of tendon lesions treated with RGTA in horses (Monocentric uncontrolled study on spontaneous cases)", Ecole Nationale Vétérinaire de Maison Alfort. Feb. 2009.
Turino et al., "Hyaluronan in respiratory injury and repair", Am J Respir Crit Care Med. May 1, 2003;167(9):1169-75.
European Search Report mailed Aug. 1, 2019 for EP Application No. 19305095.2.
European Search Report mailed Jun. 15, 2020 for EP Application No. 201161781.8.
Campo et al. "The antioxidant and antifibrogenic effects of the glycosaminoglycans hyaluronic acid and chondroitin-4-sulphate in a subchronic rat model of carbon tetrachloride-induced liver fibrogenesis." Chemico-Biological Interactions 2004;148:125-138.
Galluccio et al., "Short-term effect of the combination of hyaluronic acid, chondroitin sulfate, and keratin matrix on early symptomatic knee osteoarthritis", European Journal of Rheumatology, vol. 2, Issue 3, Sep. 2015, pp. 106-108.
Groß et al., "Comparative study of 0.1% hyaluronic acid versus 0.5% carboxymethylcellulose in patients with dry eye associated with moderate keratitis or keratoconjunctivitis", Clinical ophthalmology, Jun. 2018, pp. 1081-1088.
Limberg et al., "Topical Application of Hyaluronic Acid and Chondroitin Sulfate in the Treatment of Dry Eyes", American Journal of Ophthalmology vol. 103, Issue 2, Feb. 1987, pp. 194-197.
Office Action received for Israeli Patent Application No. 284995, mailed on Jan. 26, 2025, 9 pages.
Wang et al., "Cross-linked collagen-chondroitin sulfate-hyaluronic acid imitating extracellular matrix as scaffold for dermal tissue engineering", Tissue Engineering Part C: Methods, vol. 16, Issue 2, Apr. 2010, pp. 269-279.
Wang et al., "The effect of gelatin-chondroitin sulfate-hyaluronic acid skin substitute on wound healing in SCID mice", Biomaterials, vol. 27, Issue 33, Nov. 2006, pp. 5689-5697.
Zuijdendorp et al., "Significant reduction in neural adhesions after administration of the regenerating agent OTR4120, a synthetic glycosaminoglycan mimetic, after peripheral nerve injury in rats", Journal of neurosurgery, vol. 109, Issue 5, Nov. 2008, pp. 967-973.
Handbook of Experimental Pharmacology, 2012, vol. 207, p. 361-383.
Japanese Office Action issued in Japanese Application No. 2024-131744 dated Sep. 26, 2025.

* cited by examiner

| Famille de produits RGTA OTR412 | Famille de produit OTR413 |
| --- | --- |
| 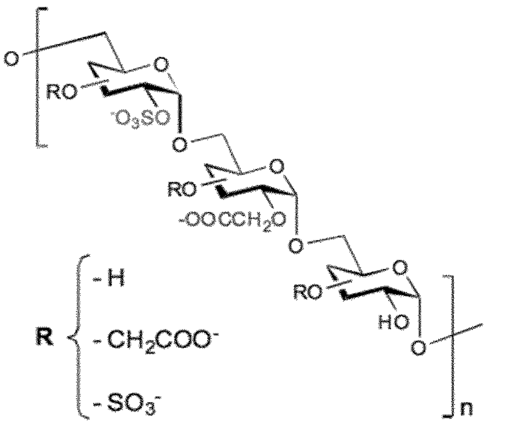 | 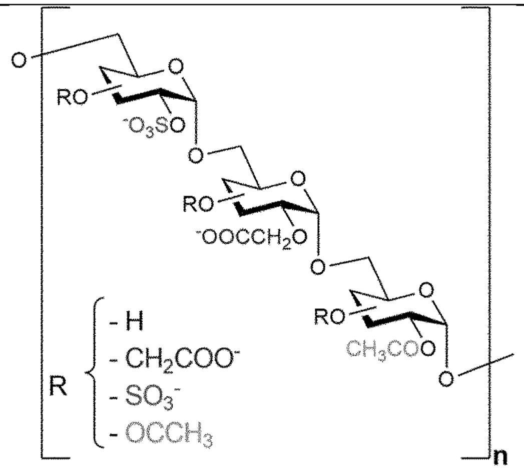 |

COSMETIC/DERMATOLOGICAL COMPOSITION

CROSS-REFERENCE TO RELATED APPLICATIONS

The present Application for Patent is a National Stage Entry of International Application PCT/EP2019/087146, filed Dec. 30, 2019, which claims priority to European Patent Application No. 19305095.2, filed Jan. 24, 2019. The disclosures of the priority applications are incorporated in their entirety by reference herein.

TECHNICAL FIELD

The present invention relates to a pharmaceutical or dermatological composition, and to the use thereof as a medicament or medical device.

The present invention also relates to a cosmetic or dermatological composition, as well as to a care kit comprising the composition of the invention.

The present invention also relates to an anti-aging cosmetic or dermatological composition, as well as to a care kit comprising the composition of the invention.

The present invention also relates to a cosmetic, dermatologically hydrating composition, as well as to a care kit comprising the composition of the invention.

The present invention also relates to an ophthalmological composition, in particular an ophthalmological composition which hydrates the cornea, as well as to a care kit comprising the composition of the invention.

The present invention also relates to an anti-wrinkle cosmetic or dermatological composition, as well as to a care kit comprising the composition of the invention.

The present invention also relates to a cosmetic or dermatological composition for the use thereof in the treatment of skin aging, for improving the appearance of the skin, as well as to a care kit comprising the composition of the invention.

The present invention is used in particular in the cosmetic, pharmaceutical and veterinary fields.

The present invention is used in particular in the articulatory pharmaceutical and veterinary fields, in particular for improving and for facilitating the movement and recovery of the motor functions.

The present invention is used in particular in the pharmaceutical and veterinary fields of vertebrae movement, in particular for improving and for facilitating the movement and recovery of the motor functions.

The present invention is used in the dental field, in particular in improving gums and buccal mucous membranes, fibroses, for example muscle fibroses, adhesions, fibroses of the digestive system, fibroses associated with surgery, heart fibroses, brain fibroses, as an antioxidant, for example for treatment of oxidative stress.

In the description below, the references between square brackets [ ] refer to the list of references set out at the end of the text.

PRIOR ART

More than an external casing, the skin is an organ in its own right, which plays an essential role not only in protecting the body against external aggressions, but also at the esthetic and emotional level. The skin breathes, it is sensitive to external aggressions, and it reacts to our general state of health as well as to the hormonal balance.

The human skin is made up of two components—the epidermis and the dermis. The hypodermis or subcutaneous connective tissue, of very variable thickness, is often functionally attached to the skin and is essentially made up of very vascularized and innervated adipose tissues which function as an interface to the underlying muscles and tendons. Fit the sweat and sebaceous glands, the skin appendages, hairs, and nails.

A healthy skin is a well hydrated skin. It is soft, firm, supple and elastic. The dermis is made up of a cellular structure, the main aim of which is to ensure the hydration of our skin. In the epidermis, the lamellae of the cornea cells, protective keratin compounds in the form of "mille feuilles" function as a barrage for retaining the water and filtering the evaporation thereof. The skin is made up of approximately 70% water, i.e. ⅕ of the water stored in our body. The water circulates from the dermis towards the epidermis. A cellular cushion made up of lipid-based fatty material, and more particularly ceramides, prevents the water from evaporating. This is what determines the natural hydration factor of our epidermis. Well hydrated skin has a normal hydration rate of between 13% and 15%. When this rate drops to 10%, the skin is dehydrated. When the epidermis is not correctly hydrated, due to a lack of water or essential fatty acids, the skin loses its suppleness and becomes dull.

The first visible signs linked to age appear in the texture, the suppleness, the color, the transparency, and the appearance of wrinkles.

In the field of facial aesthetics, the changes in the skin linked to age and to hormone regulation are typically identified as atrophy, a relaxation and fattening of the skin. Atrophy corresponds to the significant thinning of the dermis and of the epidermis, resulting in a reduction of the number of layers of cells of the epidermis, and in the thickness of the dermal connective tissue, the relaxation of the hypodermis and the subcutaneous tissues (fats, muscles), resulting in excess skin and ptosis. The relaxation by visible slumping in the region of the cheeks and jawline, as well as under the eyelids; as for thickening associated with a weight increase with age, this is observed by swelling of the bottom of the face and of the neck.

These signs of aging linked to time may be accelerated and amplified by the lifestyle, such as in particular abuse of tobacco, alcohol, or exposure to the sun. They are also often accompanied by a dryness and a redness of the skin, associated with a loss of elasticity resulting in an alteration of the quality of the cutaneous tissue. The skin forms folds under mechanical pressures, and takes longer to recover and return to its initial state. These visual signs are simply the outer reflection of these internal changes associated with the age of the organization of the skin.

The reduction in the thickness of the epidermis with age results in a reduction in the multiplication of the cells of the base layer, a reduction in the number of layers of epidermal cells, an alteration in the quantitative, structural, organizational and functional extracellular matrix, both on the proteins and on the glycosaminoglycans (GAGs) and proteoglycans (PGs), and the appearance of wrinkles.

Among these (GAG), hyaluronic acid (HA) plays a central role in maintaining the hydration at all the levels of the layers of the skin, and its reduction is correlated with the appearance of wrinkles and with the heparan sulfates (HS) in the regulation of the natural equilibrium of the tissue homeostasis, ensuring a quadruple role as an element for stabilization, protection of the matrix architecture, storage, and regulation of the bioavailability of the cellular communication factors in the microenvironment, both in the epidermis and in the dermis or hypodermis.

With the aim of reducing the unattractive effects linked to the alterations and aging of the skin, numerous approaches have sought to prevent, delay, improve the various elements, both protein and GAGs, present in the skin. This may in particular be an approach for attempting to bring about an increase in the synthesis thereof, delaying their degradation, by introducing products which are capable of substituting the endogenic products but are more resistant to degradation, or the introduction of stimulants of the synthesis of the proteins of the matrix, such as the collagens or elastin, also improves the performance of the skin at the mechanical and aesthetic level. Another possibility is that of using surface active agents, which also has immediately visible effects on the skin, reducing lines and wrinkles and smoothing the skin, but these effects are very short-term and superficial.

There are numerous cosmetic compositions in the prior art, active ingredients for treating the aging of the skin. However, none of these compositions, or none of these active ingredients, makes it possible to act in a lasting manner on the signs of aging, and/or to make it possible to naturally restore/improve the structure of the skin.

There is therefore a real need, in the prior art, to find a compound and/or a composition which makes it possible to effectively treat the cutaneous aging and/or to improve the appearance of the skin in a lasting manner, and/or which improves the structure of the skin.

There are also numerous cosmetic compositions, active ingredients for treating the aging of the skin, the effect and/or benefit of which is time-limited, in particular due to the natural elimination speed thereof, and/or associated with the environment, thus limiting the duration of the effect which is linked to the presence thereof in the region to be treated and/or on the skin.

There is therefore a real need, in the prior art, to find a compound and/or a composition of which the effect and/or the benefit is longer-term, in particular a compound and/or a composition which is capable of making it possible to effectively treat cutaneous aging and/or to improve the appearance of the skin in a lasting manner, and/or which improves the structure of the skin.

Furthermore, the known compositions and/or active ingredients do not make it possible to effectively restore and/or improve the structure of the skin. In particular, the known compositions and/or active ingredients do not make it possible to restore and/or improve the structure of the skin, and/or to effectively prevent the aging of the skin.

Moreover, in order to be relatively effective the known compositions and/or active ingredients require a significant number of applications, and/or a long treatment duration, and/or a high application frequency, in particular on the skin. The significant number of applications and/or the significant/long treatment duration may possibly result in sensitizing the skin and cause possible allergic reactions.

There is therefore a real need, in the prior art, to find a compound and/or a composition which makes it possible to effectively treat the cutaneous aging and/or to improve the appearance of the skin which in particular allows for a limited number of applications in order to achieve an effect, in particular anti-aging and/or an improvement in the appearance of the skin.

Moreover, the known compositions and/or active ingredients generally have a superficial effect, for example simply temporary, for example for a few hours, which does not allow for a lasting and/or structural effect. Furthermore, the known compositions and/or active ingredients do not make it possible to treat and/or compensate the mechanisms and/or flaws resulting from cutaneous aging.

For example, hyaluronic acid is used in the cosmetics field as a hydrating compound, and also in the medical field, for example for treating vaginal or vulval dryness. Hyaluronic acid is used in particular by means of injection, for example in the region of the labia, in order to reinflate and rehydrate the skin and restore volume to the labia majora which can again protect the vulva and the vaginal opening, and also prevent the itching associated with this dryness. Hyaluronic acid is also used in injection for treating dry eyes, dry hair, and for rehydration of hair follicles, for example in the form of gel or by micro-injection, for example in mesotherapy alone or together with nourishing or protective cofactors. Hyaluronic acid can also be used in injection for improving the sex life of men, by increasing their gland. Examples of applications and/or uses of hyaluronic acid are shown in particular in the following documents: Modified hyaluronic acid based materials for biomedical applications. Tiwari S, Bahadur P. Int J Biol Macromol. 2019 January; 121:556-571. doi: 10.1016/j.ijbiomac.2018.10.049. Epub 2018 Oct. 12. Review [1]; Hyaluronic acid, a promising skin rejuvenating biomedicine: A review of recent updates and pre-clinical and clinical investigations on cosmetic and nutricosmetic effects. Bukhari S N A, Roswandi N L, Waqes M, Habib H, Hussain F, Khan S, Sohail M, Ramli N A, Thu H E, Hussain Z. Int J Biol Macromol. 2018 December; 120 (Pt B):1682-1695. doi: 10.1016/j.ijbiomac.2018.09.188. doi: 10.1016/j.ijbiomac.2018.09.188 [2], and Reduction of post-operative adhesion development. Diamond M P. Fertil Steril. 2016 October; 106(5):994-997.e1. doi: 10.1016/j.fertnstert.2016.08.029. Epub 2016 Sep. 10. Review [3]. However, although it has a number of applications, hyaluronic acid is used in injection, which requires a doctor and a precise medical procedure which cannot be performed daily by a user.

There is therefore a real need, in the prior art, to find a compound and/or a composition which makes it possible to effectively treat the dryness of tissues, in particular cutaneous, in particular a compound and/or a composition, by local application, for example by simple application to the tissue, for example cutaneous.

There is therefore a real need, in the prior art, to find a compound and/or a composition which makes it possible to effectively treat the aging of the skin, and/or which makes it possible to improve the appearance of the skin, by local application, for example by simple application to the tissue, for example cutaneous.

It is also known that, over time, the tissues, in particular the skin, undergo a slow and irreversible development leading to anatomical, histological, and functional changes.

There are numerous cosmetic compositions in the prior art, active ingredients for treating the aging of the skin. However, none of these compositions, or none of these active ingredients, makes it possible to act and/or to have a significant effect on the mechanism(s) involved in the anatomical, histological and/or functional changes of the tissues, in particular of the skin.

There is therefore a real need, in the prior art, to find a compound and/or a composition which makes it possible to act and/or to have a significant effect on the mechanism(s) involved in the anatomical, histological and/or functional changes of the tissues, in particular of the skin.

Compounds exist in the prior art which are used in the therapeutic field and are capable of improving the tissue environment, for example biocompatible polymers, in particular RGTA is known by a person skilled in the art to have an effect on a tissue repair and regeneration process by acting on the extracellular matrix, in particular possible protection of protein elements of the cellular and tissue microenvironment. They are also known for properties which are also soothing and pain-relieving, and possibly anti-fibrosis activities (patent document US06689741, US2014301972A1 [4], Reversal of abnormal collagen production in Crohn's disease intestinal biopsies treated with regenerating agents. Alexakis C, Caruelle J P, Sezeur A, Cosnes J, Gendre J P, Mosnier H, Beaugerie L, Gallot D, Malafosse M, Barritault D, Kern P. Gut. 2004 January; 53(1):85-90 [5]), antioxidant (Insights on a new path of pre-mitochondrial apoptosis regulation by a glycosaminoglycan mimetic. Yue X L, Lehri S, Li P, Barbier-Chassefière V, Petit E, Huang Q F, Albanese P, Barritault D, Caruelle J P, Papy-Garcia D, Morin C. Cell Death Differ. 2009 May; 16(5):770-81. doi: 10.1038/cdd.2009.9 [6], Differential effect triggered by a heparan mimetic of the RGTA family preventing oral mucositis without tumor protection. Mangoni M, Yue X, Morin C, Violot D, Frascogna V, Tao Y, Opolon P, Castaing M, Auperin A, Biti G, Barritault D, Vozenin-Brotons M C, Deutsch E, Bourhis J. Int J Radiat Oncol Biol Phys. 2009 Jul. 15; 74(4):1242-50. doi: 10.1016/j.ijrobp.2009.03.006 [7]), healing (RGTA OTR4120, a heparan sulfate mimetic, is a possible long-term active agent to heal burned skin. Garcia-Filipe S, Barbier-Chassefiere V, Alexakis C, Huet E, Ledoux D, Kerros M E, Petit E, Barritault D, Caruelle J P, Kern P J Biomed Mater Res A. 2007 January; 80(1):75-8) promoting cutaneous healing, and for treatment of pain (patent document EP1677807 [9]).

These activities may in particular be due to a capacity for these compounds to inhibit certain glycanases, for example heparanase, heparitinases, Chondroitinases and Hyaluronidases (Heparin-like synthetic polymers, named RGTAs, mimic biological effects of heparin in vitro. Rouet V, Meddahi-Pellé A, Miao H Q, Vlodaysky I, Caruelle J P, Barritault D. J Biomed Mater Res A. 2006 Sep. 15; 78(4):792-7 [10], EP1677807 [9], patent document US06689741, US2014301972A1 [4]), for elastase inhibition (FGF protection and inhibition of human neutrophil elastase by carboxymethyl benzylamide sulfonate dextran derivatives. Meddahi A, Lemdjabar H, Caruelle J P, Barritault D, Hornebeck W. Int J Biol Macromol. 1996 February; 18 (1-2):141-5 [11], collagenases, plasmin (Human plasmin enzymatic activity is inhibited by chemically modified dextrans. Ledoux D, Papy-Garcia D, Escartin Q, Sagot M A, Cao Y, Barritault D, Courtois J, Hornebeck W, Caruelle J P. J Biol Chem. 2000 Sep. 22; 275(38):29383-90 [12]) and the activator of plasminogen or calpain (Heparan sulfate mimetics modulate calpain activity during rat Soleus muscle regeneration. Zimowska M, Szczepankowska D, Streminska W, Papy D, Tournaire M C, Gautron J, Barritault D, Moraczewski J, Martelly I. J Cell Physiol. 2001 August; 188(2):178-87 [13]), for protection in the region of the sites to which they bind (sites described in the literature as binding site for heparin sulfates or "Heparan/heparin binding sites") of the matrix proteins (growth and cellular communication factors, i.e. VEGF and TGFbeta (RGTA® or ReGeneraTing Agents mimic heparan sulfate in regenerative medicine: from concept to curing patients. Barritault D, Gilbert-Sirieix M, Rice K L, Siñeriz F, Papy-Garcia D, Baudouin C, Desgranges P, Zakine G, Saffar J L, van Neck J. Glycoconj J. 2017 June; 34(3):325-338. doi: 10.1007/s10719-016-9744-5 [14].

However, the RGTAs are used in particular during treatment of significant lesions and, in general, remain expensive compounds which cannot be used in a usual manner, in particular in cosmetics.

There is therefore a real need to find a new compound, a new composition, or treatment, making it possible to treat the aging of tissues, in particular of the skin, and/or to increase the effectiveness of treatment of the known compositions, while also reducing the cost thereof.

There is therefore a real need, in the prior art, to find a compound and/or a composition which makes it possible to act and/or to have a significant effect on the mechanism(s) involved in the anatomical, histological and/or functional changes of the tissues, in particular of the skin, associated with aging, while also having a reduced cost.

DESCRIPTION OF THE INVENTION

The present invention specifically aims to meet these needs by providing a pharmaceutical composition, preferably a cosmetic or dermatological composition, comprising a biocompatible polymer of the general formula (I) below $$AaXxYy \qquad (I)$$

in which:

A represents a monomer,

X represents an $-R_1COOR_2$ or $-R_9(C{=}O)R_{10}$ group,

Y represents an O or N-sulfonate group complying with one of the following formulae: $-R_3OSO_3R_4$, $-R_5NSO_3R_6$, $R_7SO_3R_8$ in which:

$R_1$, $R_3$, $R_5$ and $R_9$ independently represent an aliphatic hydrocarbon chain, optionally branched and/or unsaturated, and which optionally contains one or more aromatic cycles with the exception of benzylamine and benzylamine sulfonate, $R_2$, $R_4$, $R_6$ and $R_8$ independently represent a hydrogen atom or a cation, $R_7$ and $R_{10}$ independently represent a bond, an aliphatic hydrocarbon chain, optionally branched and/or unsaturated, "a" represents the number of monomers, "x" represents the rate of substitution of the monomers A by the groups X, "y" represents the rate of substitution of the monomers A by the groups Y, and hyaluronic acid.

Advantageously, the inventor has surprisingly demonstrated that the association of biocompatible polymers of general formula (I) as defined above, also referred to as RGTA in the present document, and hyaluronic acid, makes it possible to treat and/or prevent aging of biological tissues in a synergic manner.

In particular, the inventor has demonstrated that the composition according to the invention advantageously makes it possible to prevent, reduce, eliminate or limit the effects of age on the appearance of the skin, whether the aging be chronobiologic, or accelerated, for example due to external aggressions, for example due to radiation, for example UVA, UVA, and/or ionizing rays.

The inventor has also surprisingly demonstrated that the effects achieved are visible and lasting. In particular, the inventor has demonstrated that the composition according to the invention advantageously allows for a visible and lasting reduction in the signs and markers of aging, for example a reduction in lines and wrinkles, advantageously making it possible to improve the appearance of the skin, which may advantageously appear younger, or a more beautiful skin, for example a brighter skin, a more supple, firmer and also tighter skin.

In particular, the inventor has demonstrated that the composition according to the invention advantageously makes it possible to protect the tissues, for example the skin and/or mucous membranes, from external aggressions, for example due to exposure to radiation, for example UVA, UVA, and/or ionizing rays, to the cold, etc. In particular, the inventor has demonstrated that the composition according to the invention advantageously makes it possible to prevent and/or to protect the tissues, for example the skin and/or the mucous membranes, from dryness. For example, the inventor has demonstrated that the composition according to the invention advantageously synergistically exhibits effects of protection and/or hydration of the mucous membranes, and advantageously makes it possible to reduce the effects associated with tissue dryness.

The inventor has also demonstrated that the composition according to the invention advantageously makes it possible, in particular by improving the properties of the tissues, for example hydration, suppleness, etc., to facilitate the articular and tendinous movements, to improve the intervertebral movements, in particular by improving the properties of the intervertebral discs and, in a general manner, promoting the functional recovery of the tissues.

Furthermore, the inventor has demonstrated that the combination of biocompatible polymers of general formula (I) with hyaluronic acid according to the invention can be used/applied whatever the biological tissues, for example by means of local application, for example by means of cutaneous application and/or application to the surface of the biological tissues. Furthermore, the inventor has demonstrated that the combination of biocompatible polymers of general formula (I) with hyaluronic acid according to the invention can also be used/applied by means of injection.

The inventor has also surprisingly and unexpectedly demonstrated that the combination of biocompatible polymers of general formula (I) with hyaluronic acid according to the invention exhibits a strong synergic effect observed in the functional recovery of tissues and recovery thereof from scarring.

Furthermore, the inventor has also surprisingly and unexpectedly demonstrated that the combination of biocompatible polymers of general formula (I) with hyaluronic acid according to the invention has a synergic effect in the treatment of scarring, for example the treatment of scars, and the esthetic treatment of scars.

Moreover, the inventor has surprisingly demonstrated that the combination of biocompatible polymers of general formula (I) with hyaluronic acid according to the invention has a lasting effect over time, and in particular makes it possible to extend both the duration of action of the combination, by slowing the elimination, and advantageously furthermore allows for restoration of the synthesis and/or production of biological elements, for example proteins, which make up the extracellular matrix, the production of which is reduced and/or altered with aging, for example the biological tissue.

In the present document, "tissue" means any biological tissue of a mammal that is known to a person skilled in the art. This may for example be connective tissue, muscle tissue, nerve tissue, bone tissue, cartilage tissue, and/or epithelial tissue. It may, for example, be any biological tissue of any organ or organelle of a mammal known to a person skilled in the art. It may for example be tissue of the digestive tract, tissue of the gastrointestinal tract, of the food and excretion digestive system, of the genital tract, of the reproductive system, of the optical, olfactive or auditory system, of the sensory system, of the circulatory and/or cardiovascular system, of the respiratory system, of the muscular system, of the locomotive system. It may for example be gastric tissue, buccal tissue, the cornea, tympanic tissue, tissue of the cochlea, of the skin, bone tissue, cartilage tissue, tendinous tissue, nerve tissue, bone marrow, nerve fiber, the retina, arteries and/or vessels, tissue of the renal or urinary digestive system, and/or any biological tissue which allows for biological fluids to pass through, for example any biological tissue allowing for passage of biological fluids which is known to a person skilled in the art, for example the Schlemm canal or the lymphatic system.

In the present document, "scarring" means any tissue response to an aggression of any type, duration or intensity, which results in an inflammation and the formation of scar tissue which is not identical to the original tissue. It may, for example, be any formation of scar tissue, not identical to the original tissue, known to a person skilled in the art. It may for example be scar tissue not identical to the original tissue, in which there is formation of a mark and/or fibrosis, for example having aspects and properties which are different from the original tissue, in terms of shape, suppleness, adhesion and/or thickness.

In the present document, monomer means for example a monomer selected from the group comprising sugars, esters, alcohols, amino acids, or nucleotides.

In the present document, the monomers A making up the base elements of the polymers of formula I may be identical or different.

In the present document, the monomers A may independently be monomers of the following formula:

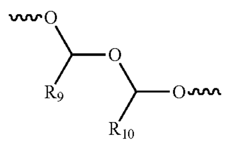

in which $R_9$ and $R_{10}$ independently represent an oxygen atom, an aliphatic hydrocarbon chain, optionally branched and/or unsaturated, a heteroaryl group independently comprising one or more oxygen and/or nitrogen atoms, an aldehyde function, a carboxylic acid group, a diol, a substituted diol, a group of formula $—R_{11}—(X)_n—R_{12}$ in which $R_{11}$ represents a $C_1$ to $C_4$ aliphatic carbon chain, optionally branched and/or unsaturated, X represents a heteroatom selected from oxygen and nitrogen, n is an integer of between 1 and 4, and $R_{12}$ is a hydrogen atom, an aliphatic hydrocarbon chain, optionally branched and/or unsaturated, a heteroaryl group independently comprising one or more oxygen and/or nitrogen atoms, an aldehyde function, a carboxylic acid group, a diol, a substituted diol.

In the present document, the monomer association may make it possible to form a polymer backbone, for example a polymer backbone of the polyester, polyalcohol or polysaccharide type, of the nucleic acid or protein type.

In the present document, the polyesters may for example be copolymers of biosynthesis or chemical synthesis, for example aliphatic polyesters or polyesters of natural origin, for example polyhydroxyalconaotes.

In the present document, the polysaccharides and the derivatives thereof may be of bacterial, animal, fungal, and/or plant origin. They may for example be single-chain polysaccharides, for example polyglucoses, for example dextran, cellulose, beta glucan, or other monomers comprising more complex units, for example xanthans, for example glucose, mannose, and glucuronic acid, or indeed glucuronanes and glucoglucuronane.

In the present document, the polysaccharides of plant origin may be single-chain, for example cellulose (glucose), pectins (galacturonic acid), funcanes, starch, or more complex such as alginates (galuronic and mannuronic acid).

In the present document, the polysaccharides of fungal origin may be steroglucan for example.

In the present document, the polysaccharides of animal origin may be chitins or chitosan (glucosamine) for example.

In the present document, the monomers A making up the base elements of the polymers of formula I may advantageously be identical.

In the present document, the monomers A making up the base elements of the polymers of formula I may advantageously be glucose.

The number of monomers A defined in formula (I) by "a" may be such that the mass of said polymers of formula (I) is approximately between 2000 and 6000 Daltons, for example corresponding to at least 10 monomers of glucose. For example the mass of said polymers of formula (I) may be approximately between 3000 Daltons and 6000 Daltons, for example corresponding to 12 to 20 monomers of glucose.

The number of monomers A defined in formula (I) by "a" may also be such that the mass of said polymers of formula (I) is less than approximately 2,500,000 Daltons (corresponding to 7000 monomers of glucose). Advantageously, the mass of said polymers of formula (I) may be between 3000 and 250,000 Daltons, for example from 3000 to 6000 Daltons, or for example from 20,000 to 250,000 Daltons, or for example from 75,000 to 150,000 Daltons.

In the present document, in the group $—R_1COOR_2$ representing X, $R_1$ may be a $C_1$ to $C_6$ alkyl, for example a methyl, an ethyl, a butyl, a propyl, a pentyl, preferably a methyl group, and $R_2$ may be a bond, a $C_1$ to $C_6$ alkyl, for example a methyl, an ethyl, a butyl, a propyl, a pentyl, an $R_{21}R_{22}$ group in which $R_{21}$ is an anion and $R_{22}$ is a cation selected from the group of the alkali metals.

The group X is preferably the group of formula $—R_1COOR_2$ in which $R_1$ is a $—CH_2—$ methyl group and $R_2$ is an $R_{21}R_{22}$ group in which $R_{21}$ is an anion and $R_{22}$ is a cation selected from the group of alkali metals, preferably the group X is a group of formula $—CH_2—COO^-$ or carboxymethyl.

In the present document, in the group $—R_9(C{=}O)R_{10}$ representing X, $R_9$ may be a $C_1$ to $C_6$ alkyl, for example a methyl, an ethyl, a butyl, a propyl, a pentyl, preferably a methyl group, and $R_{10}$ may be a bond, a $C_1$ to $C_6$ alkyl, for example a methyl, an ethyl, a butyl, a propyl, a pentyl, a hexyl.

The rate of substitution of all the monomers A by the groups X defined in the general formula (I) by "x" may be of from 10 to 150%, from 40 to 80%, and preferably of the order of 50% or 60%.

In the present document, in the group corresponding to one of the following formulae $—R_3OSO_3R_4$, $—R_5NSO_3R_6$, $—R_7SO_3R_8$ and representing Y, $R_3$ may be a bond, a $C_1$ to $C_6$ alkyl, for example a methyl, an ethyl, a butyl, a propyl, a pentyl, preferably a methyl group, $R_5$ may be a bond, a $C_1$ to $C_6$ alkyl, for example a methyl, an ethyl, a butyl, a propyl, a pentyl, preferably a methyl group, $R_7$ may be a bond, a $C_1$ to $C_6$ alkyl, for example a methyl, an ethyl, a butyl, a propyl, a pentyl, preferably a methyl group, $R_4$, $R_6$ and $R_8$ may independently be a hydrogen atom or a cation $M^+$, for example $M^+$ may be an alkali metal.

The group Y is preferably the group of formula $—R_7SO_3R_8$ in which $R_7$ is a bond and $R_8$ is an alkali metal selected from the group comprising lithium, sodium, potassium, rubidium, and cesium. The group Y is preferably an $—SO_3^-$, $—SO_3^-$, $Na^+$ group.

The rate of substitution of all the monomers A by the groups Y defined in the general formula (I) by "y" may be of from 10 to 170%, from 30 to 150%, from 55 to 160%, from 55 to 85%, from 120 to 160%, and preferably of the order of 70, 140 or 150%.

In the present document, in the definition of the rates of substitution above, a rate of substitution "x" of 100% means that each monomer A of the polymer of the invention statistically contains one group X. In the same way, a rate of substitution "y" of 100% means that each monomer of the polymer of the invention statistically contains one group Y. The rates of substitution above 100% indicate that each monomer statistically bears more than one group of the type considered; vice versa, the rates of substitution of less than 100% indicate that each monomer statistically bears less than one group of the type considered.

The polymers may also comprise chemically functional groups, denoted Z, which are different from X and Y.

In the present document, the groups Z may be identical or different and may be independently selected from the group comprising amino acids, fatty acids, fatty alcohols, ceramides, or derivatives thereof, or addressing nucleotide sequences.

The groups Z may also represent identical or different active agents. These may for example be therapeutic agents, diagnostic agents, an anti-inflammatory, an antimicrobial, an antibiotic, a growth factor, an enzyme, an antioxidant compound, polyphenols, tannins, anthocyanins, lycopenes, terpenoids, and resveratrol.

In the present document, the group Z may advantageously be a saturated or unsaturated fatty acid. It may for example be a fatty acid selected from the group comprising acetic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, trans-vaccenic acid, linoleic acid, linolelaidic acid, $\alpha$-linoleic acid, $\gamma$-linoleic acid, dihomo-$\gamma$-linoleic acid, arachidonic acid, eicosapentaenoic acid, clupanodonic acid, or docosahexaenoic acid. The fatty acid is preferably acetic acid.

In the present document, the group Z may advantageously be an amino acid of the series L or D, selected from the group comprising alanine, asparagine, an aromatic chain for example tyrosine, phenylalanine, tryptophane, thyroxine, or histidine. The amino acid is preferably phenylalanine.

In the present document, the group Z may be an antioxidant, for example vitamin A, C, E, B9, B6, glutathione, selenium, polyphenols, for example catechins, for example green tea, flavonoids, tannins, anthocyanins, for example red fruits, lycopenes, terpenoids, and resveratrol.

In the present document, the group Z may be anti-aging compounds, for example retinoids.

The groups Z may advantageously provide the polymers with additional biological or physicochemical properties. For example, the groups Z may increase the solubility or the lipophily of said polymer which allows for example for improved diffusion or tissue penetration.

The groups Z may advantageously provide the polymers with additional biological or physicochemical properties. Thus, the polymers of the invention, for example when the group Z is selected from an antioxidant compound, an anti-aging compound, the polymers of the invention may advantageously transport said compounds and thus provide an additional and/or supplementary biological effect.

Polymers in which Z is present comply with the following formula II:

Aa Xx Yy Zz (II)

in which A, X, Y, a, x, y are as defined above, and z represents the rate of substitution by the groups Z.

In the present document, the rate of substitution by the groups Z represented by "z" may be from 1 to 50%, from 10 to 25%, preferably 15, 20 or 25%.

The X, Y and Z groups may be independently bonded to the monomer A, and/or independently bonded to one another. When at least one of the groups X, Y and Z is independently bonded to a group X, Y and Z that is different from the first, one of said groups X, Y or Z is bonded to the monomer A.

Thus, the groups Z may be bonded by covalence directly to the monomers A, or bonded by covalence to the groups X and/or Y.

In the present document, the groups Z may also be conjugated to the polymers of formula AaXxYy by bonds other than covalent, for example by ionic bonds, for example via ionic interactions, hydrophilic bonds, or hydrophobic bonds. The polymers of the invention may thus form a vectorization system of Z.

In the present document, the polymer may for example be an RGTA selected from the group comprising the compounds OTR4120, OTR41201, OTR41202, OTR41203, OTR41205, OTR41210 OTR41301, OTR41302, OTR41303, OTR41305, OTR 41310, OTR3131.

In the present document, the polymer may for example be an RGTA selected from the group comprising the compounds OTR41201, OTR41202, OTR41203, OTR41205, OTR41210, OTR4120, OTR4122, OTR4125, OTR41301, OTR41302, OTR41303, OTR41305, OTR41310, OTR3131, OTR4132, OTR4135, OTR415 having the features mentioned in table 1 below.

biocompatible polymer with respect to the total volume of the composition.

In the present document, the composition may be formulated and/or adapted according to the administration thereof. For example, for topical administration the composition may comprise from 0.1 to 100 μg/mL by weight of biocompatible polymer with respect to the total volume of the composition.

For example, for parenteral administration, the composition may be administered in order to deliver a dose of biocompatible polymer of between 0.1 and 5 mg per kilogram of body weight.

The molecular weight of the biocompatible polymers present in the composition may advantageously be selected depending on the administration path of the composition, and on the target, for example epidermis, dermis mucous membranes, cornea, tympanic membrane, organs, intra-articular liquid, intraocular liquid.

For example, for topical or oral administration the molecular weight may be between 3000 and 6000 Daltons in order to promote the passage of basal membranes. For example, for administration via intradermal or subcutaneous or intrathecal injection, or injection into the muscles or organs or into the intra-articular spaces, the molecular weight may be from 6000 to 2,500,000 Daltons, preferably from 20,000 to 250,000 Daltons, and for example from 75,000 to 150,000 Daltons.

Advantageously, when the molecular weight of the biocompatible polymer is between 3000 and 6000 Daltons, in the case of topical application, for example on an epithelium, for example mucous membranes or the skin, it can advantageously allow for passage of the basal lamina, advantageously allowing for improved administration, and can promote an effect over a greater distance.

Advantageously, when the molecular weight of the biocompatible polymer is between 3000 and 2,500,000 Daltons,

TABLE 1

Polymers of the families Aa Xx Yy and Aa Xx Yy Zz in which A is glucose (molecular weight 180 D), X is carboxymethyl (molecular weight 58 D) Y: $SO3^-$ (molecular weight 80 D), and Z is acetate (molecular weight 43 D) or phenylalanine (molecular weight 165 D).

| Polymer Name of the RGTA | A: glucose Dextran starting polymer (molecular weight in Daltons) | Average molecular weight +/−15% | X —CH2COO % of CM/glucose substitution | Y —$SO3^-$ % of $SO_4$/glucose substitution | Z —OCCH3 % of OCCH3/glucose substitution | Z phenylalanine |
|---|---|---|---|---|---|---|
| CMDS OTR41201 | 1500 | 3000 | 60 +/− 20 | 150 +/− 20 | 0 | |
| CMDS OTR41202 | 3000 | 6000 | 60 +/− 20 | 150 +/− 20 | 0 | |
| CMDS OTR41203 | 5000 | 10,000 | 60 +/− 20 | 150 +/− 20 | 0 | |
| CMDS OTR41205 | 10,000 | 20,000 | 60 +/− 20 | 150 +/− 20 | 0 | |
| CMDS OTR41210 | 20,000 | 40,000 | 60 +/− 20 | 150 +/− 20 | 0 | |
| CMDS OTR4120 | 40,000 | 80,000 | 60 +/− 20 | 150 +/− 20 | 0 | |
| CMDS OTR4122 | 110,000 | 220,000 | 60 +/− 20 | 150 +/− 20 | 0 | |
| CMDS OTR4125 | 250,000 | 500,000 | 60 +/− 20 | 150 +/− 20 | 0 | |
| CMDS OTR41301 | 1500 | 3000 | 60 +/− 20 | 140 +/− 20 | 20 +/− 5 | |
| CMDS OTR41302 | 3000 | 6000 | 60 +/− 20 | 140 +/− 20 | 20 +/− 5 | |
| CMDS OTR41303 | 5000 | 10,000 | 60 +/− 20 | 140 +/− 20 | 20 +/− 5 | |
| CMDS OTR41305 | 10,000 | 20,000 | 60 +/− 20 | 140 +/− 20 | 20 +/− 5 | |
| CMDS OTR41310 | 20,000 | 40,000 | 60 +/− 20 | 140 +/− 20 | 20 +/− 5 | |
| CMDS OTR4131 | 40,000 | 80,000 | 60 +/− 20 | 140 +/− 20 | 20 +/− 5 | |
| CMDS OTR4132 | 110,000 | 220,000 | 60 +/− 20 | 140 +/− 20 | 20 +/− 5 | |
| CMDS OTR4135 | 250,000 | 500,000 | 60 +/− 20 | 140 +/− 20 | 20 +/− 5 | |
| CMDS OTR415 | | 5000 | 60 +/− 20 | 70 +/− 15 | — | 15 +/− 5 |

In the present document, the composition may have a concentration of from 0.1 to 100 μg/mL by weight of biocompatible polymer with respect to the volume of the composition. For example, the composition may have a preferred concentration of from 1 to 10 μg/mL by weight of it can advantageously allow for improved availability and lifetime, whatever the tissue location.

In the present document "hyaluronic acid" means any hyaluronic acid known to a person skilled in the art, for example a non-sulfated linear glycosaminoglycan made up of repeated units of D-glucuronic acid and N-acetyl-D-glucosamine. It may for example be hyaluronic acid (HA) in the acid form thereof or in the form of a salt (hyaluronate), cross-linked hyaluronic acid. The HA is a non-sulfated linear glycosaminoglycan made up of repeated units of D-glucuronic acid and N-acetyl-D-glucosamine (Tammi R., Agren U M., Tuhkanen A L., Tammi M. Hyaluronan metabolism in skin. Progress in Histochemistry & Cytochemistry. 29(2):1-81, 1994 [15]). It may for example be hyaluronic acid having average molecular weight fractions of from 5000 to 3,000,000 Daltons, preferably between 50,000 and 2,000,000 Daltons. In the present document, the hyaluronic acid may be obtained by any method known to a person skilled in the art. These may for example be methods described in the review Hyaluronan fragments: an information-rich system (R. Stern et al., European Journal of Cell Biology 58 (2006) 699-715 [16]). It may also be natural or modified hyaluronic acid, which is commercially available, whatever the designations and/or molecular weight thereof, for example commercial hyaluronic acid selected from Hyactive CPN; Cristalhyal; Nutra HA; Oligo HA; D Factor; Hyaluderm; juvelift; Restylane; Revitacare, this list not being exhaustive. It may also be hyaluronic acid marketed by the company Contipro (https://www.contipro.com/portfolio/manufacturer-of-anti-ageing-cosmetic-raw-materials/HyActive) and/or Givaudan (https://www.givaudan.com/fragrances/active-beauty/products/cristalhyal%C2%AE-range).

In the present document, the composition may have a concentration of from 0.1 to 5 wt. % hyaluronic acid with respect to the total weight of the composition. For example, the composition may have a concentration of from 0.5 wt. % to 2.5 wt. % hyaluronic acid with respect to the total weight of the composition.

In the present document, the composition may be formulated and/or adapted according to the administration thereof. For example, for topical administration the composition may comprise from 0.5 wt. % to 2.5 wt. % hyaluronic acid with respect to the total weight of the composition.

For example, for parenteral administration, for example intra-articular, for example in the synovial fluid of the knee or in the synovial fluid of the trapezo-metacarpal joint or the metacarpophalangeal joint, for example for rhizarthrosis, or for example intratendinous, for example tendinite, the composition may be administered in order to deliver a dose of from 1 mg to 20 mg hyaluronic acid per mL of composition. For example, for parenteral administration, the composition may have a concentration of from 0.1 to 20 mg/mL hyaluronic acid.

The molecular weight of the biocompatible polymers present in the composition may advantageously be selected depending on the administration path of the composition.

In the present document, "pharmaceutical composition" means any form of pharmaceutical composition that is known to a person skilled in the art. In the present document, the pharmaceutical composition may for example be a composition for topical application, an injectable solution, for example for local or systematic injection, for example in physiological serum, injectable in glucose solution, in the presence of excipients, for example dextrans, for example at concentrations known to a person skilled in the art, for example from a microgram to several milligrams per mL.

The pharmaceutical composition may for example be a medicament intended for oral administration, selected from the group comprising a liquid formulation, an oral effervescent posological form, an oral powder, a multiparticle system, an orodispersible galenic form.

For example, when the pharmaceutical composition is for oral administration, it can be in the form of a liquid formulation selected from the group comprising a solution, a syrup, a suspension, an emulsion. When the pharmaceutical composition is in the form of an oral posological effervescent, it can be in a form selected from the group comprising tablets, granules, powders. When the pharmaceutical composition is in the form of an oral powder or a multiparticulate system, it can be in a form selected from the group comprising balls, granules, mini-tablets, and microgranules. When the pharmaceutical composition is in the form of a posological orodispersible form it can be in a form selected from the group comprising orodispersible tablets, freeze-dried wafers, thin films, a chewable tablet, a tablet, a capsule, or medical chewing gum.

According to the present invention, the pharmaceutical composition may be a pharmaceutical composition for oral administration, for example via the mouth and/or sublingually, for example selected from the group comprising buccal or sublingual tablets, dental pastes, dental buccal adhesive dressings, lozenges, drops, a solution for atomization.

According to the present invention, the pharmaceutical composition may be a pharmaceutical composition for intra-urinary administration. Advantageously, when the pharmaceutical composition is suitable for intra-urinary administration it can reach the epithelium of the bladder following administration.

According to the present invention, the pharmaceutical composition may be a dermatological or cosmetic composition, for example for topical administration and/or application.

The dermatological or cosmetic composition according to the invention may comprise one or more dermatologically and/or cosmetically acceptable supports. In the present document, "dermatologically and/or cosmetically acceptable support" means any cosmetic support known to a person skilled in the art; it may for example be any cosmetic support which can be cited in the INCI (International Nomenclature of Cosmetic Ingredients) dictionary published by the PCPC (Personal Care Products Council).

The dermatological or cosmetic composition according to the invention may comprise one or more adjuvants known to a person skilled in the art. It may for example be one or more adjuvant(s) selected from agents of the ester type, hydrating agents, softening agents, mineral thickening agents, organic thickening agents, associative or otherwise, hydrosoluble and liposoluble organic solar filters, mineral solar filters, silicon compounds, scents, preservatives, ceramides and pseudo-ceramides, vitamins and provitamins, proteins, sequestrating agents, alkalizing agents, acidifying agents, reducing agents, oxidizing agents, mineral fillers, colorants, or any other adjuvant which may be cited in the INCI (International Nomenclature of Cosmetic Ingredients) dictionary published by the PCPC (Personal Care Products Council).

According to the invention, the cosmetic composition may, for example, be in any form known to a person skilled in the art. It may, for example, be an oil-in-water emulsion, water-in-oil emulsion, water-in-silicone emulsion, a multiple emulsion, a microemulsion, a nano-emulsion, a solid emulsion, an aqueous or hydro-alcoholic gel, a cream, a gel, a milk, a lotion, a cream, an oil, a balm, an ointment, a mask, a powder, an impregnated carrier, for example a transdermal patch, an impregnated dressing, an aqueous lotion, a spray, a or hydroalcoholic and/or a wax, a shampoo, a conditioner, a hair mask, serum or lotion. The cosmetic composition according to the invention may preferably be in a form selected from a cream, a gel, an ointment, an oil.

The cosmetic or dermatological composition of the invention may be obtained by any appropriate method known to a person skilled in the art for preparing a cosmetic and/or dermatological composition.

According to the present invention, the pharmaceutical composition may be a pharmaceutical composition for respiratory or nasal administration, for example in the form of an aerosol.

According to the present invention, the composition may be a composition for nasal or respiratory nasal or respiratory, for example selected from the group comprising nasal drops, nasal spray, nasal powder, aerosols, for example compressed-gas nasal aerosols and/or spray, or nebulizers.

Advantageously, when the pharmaceutical composition is suitable for nasal or via the respiratory path it can advantageously be bronchopulmonary.

According to the present invention, the composition of the present invention may be a composition for parenteral administration, for example sub-cutaneous, intramuscular, intravenous, intrathecal.

According to the present invention, the composition may be a composition for ocular administration, for example selected from the group comprising drops, gel, cream. It may for example be eyewash, for example for treatment of the cornea, by applying the composition to the surface of the eye, by trans-corneal injection, for example in the treatment of Descemet's membrane, or indeed for the treatment of glaucoma, in order to reduce the fibrosis of Schlemm's canal by injection for example into the aqueous or vitreous humor, by topical application, for example on the cornea.

Advantageously, when the composition is used in topical application on the cornea, it may advantageously be used in the trans-corneal region, advantageously if the composition comprises polymers of a low molecular weight, for example of between 2000 and 6000 Daltons.

The composition of the present invention may also comprise at least one other active ingredient, in particular another therapeutically active ingredient, for example for simultaneous or separate use, or use spread over time, according to the galenic formulation used. Said other ingredient may for example be an active ingredient used for example in the treatment of opportunistic infections, or a vitamin, or an analgesic, etc.

In the present document, the administration of the biocompatible polymer and of the hyaluronic acid may be simultaneous, successive, or concurrent.

According to the invention, at least one of the administrations may be carried out topically, orally, via a respiratory path, or by injection. The two administrations may be carried out in the same way or differently. For example, the administration of the biocompatible polymer and of the hyaluronic acid may be carried out by topical application. The administration may also be dependent on the region and/or the biological tissue to be treated.

According to the invention, the composition may, for example, be administered just once.

According to the invention, the composition may furthermore for example be administered daily, every other day, and weekly, or less often. It may for example be an administration once a day, twice a day, or less, for example once every other day, or per week.

According to the invention and the mode of administration the composition may be for example for a cream administered daily, every other day, and weekly, or less often. It may for example be an administration once a day, twice a day, or less often.

According to the invention, the composition may, for example, be administered over a period of from 1 day to 3 months, for example for 2 months. For example, the composition may be administered over a period of 3 or 6 months, for example at a daily administration frequency.

For example, when the composition is in an injectable form, the composition may be administered at an administration frequency of every 3 or 6 months or less.

The inventor has surprisingly demonstrated that the combination of a biocompatible polymer of formula AaXxYy or AaXxYyZz and natural or modified hyaluronic acid advantageously and surprisingly makes it possible to achieve a synergic effect in treatment. In particular, the inventor has demonstrated that the effect achieved was both a synergy extending beyond the individual effects of each of the compounds, and advantageously also an increase in the duration of these effects.

Furthermore, the inventor has surprisingly demonstrated that the increase in the duration of the effects could be increased yet further, for example by using a plurality of administrations, for example via identical or different administration paths, and/or a particular administration posology. For example, the administration of the composition according to the invention by injection, for example subcutaneous, intramuscular, may be followed by a cutaneous application of the composition according to the invention, for example by topical application.

In the present document, the composition according to the invention may be administered via different paths simultaneously, successively, or concurrently.

According to the invention, at least one of the administrations may be carried out topically, orally, or by injection. The two administrations may be carried out in the same way or differently. For example, the administration of the composition may be carried out by injection, followed by topical application of the composition. The administration may also be dependent on the region and/or the biological tissue to be treated.

Advantageously, when the administration of the composition may be carried out by injection, followed by topical application of the composition, the composition for topical application may be in a form selected from a cream, gel or serum.

Advantageously, the inventor has surprisingly demonstrated that the topical application of the composition in a form selected from a cream, gel or serum surprisingly makes it possible to further extend the biological effect resulting from the first administration.

The present invention also relates to a cosmetic or dermatological composition comprising a biocompatible polymer of formula AaXxYy or AaXxYyZz and natural or modified hyaluronic acid for use in non-therapeutic cosmetic treatment of cutaneous aging, lines and/or wrinkles, for protection of the scalp, and for capillary regeneration.

The biocompatible polymer is as defined above.

The hyaluronic acid is as defined above.

According to the invention, the patient may be any mammal. It may for example be an animal or a human being.

According to the invention, the mode and/or the path of administration of the biocompatible polymer may be as defined above.

According to the invention, the mode and/or the path of administration of the hyaluronic acid may be as defined above, preferably by injection into the biological tissue.

According to the invention, the frequency of administration of the biocompatible polymer may be as defined above.

According to the invention, the frequency of administration of the hyaluronic acid may be as defined above.

The present invention also relates to a cosmetic or dermatological composition comprising a biocompatible polymer of formula AaXxYy or AaXxYyZz and natural or modified hyaluronic acid for use for the non-therapeutic cosmetic prevention and/or treatment of hair loss and/or alopecia.

The biocompatible polymer is as defined above.

The hyaluronic acid is as defined above.

According to the invention, the mode and/or the path of administration of the biocompatible polymer may be as defined above.

According to the invention, the mode and/or the path of administration of the hyaluronic acid may be as defined above, preferably by injection into the biological tissue.

According to the invention, the cosmetic or dermatological composition comprising a biocompatible polymer of formula AaXxYy or AaXxYyZz and hyaluronic acid may be a composition for topical and/or capillary application, for example a cream.

According to the invention, the frequency of administration of the biocompatible polymer may be as defined above.

According to the invention, the frequency of administration of the hyaluronic acid may be as defined above.

The present invention also relates to a cosmetic or dermatological anti-aging composition and/or composition for protecting the skin from external aggressions, and/or for treatment and/or prevention of skin aging, comprising a biocompatible polymer of formula AaXxYy or AaXxYyZz and hyaluronic acid.

The biocompatible polymer is as defined above.

The hyaluronic acid is as defined above.

According to the invention, the patient may be any mammal. It may for example be an animal or a human being.

According to the invention, the mode and/or the path of administration of the biocompatible polymer may be as defined above.

According to the invention, the mode and/or the path of administration of the hyaluronic acid may be as defined above, preferably by injection into the biological tissue.

According to the invention, the frequency of administration of the biocompatible polymer may be as defined above.

According to the invention, the frequency of administration of the hyaluronic acid may be as defined above.

The present invention also relates to a cosmetic treatment method comprising application to the skin of a cosmetic composition comprising a biocompatible polymer of formula AaXxYy or AaXxYyZz and hyaluronic acid.

The biocompatible polymer is as defined above.

The hyaluronic acid is as defined above.

According to the invention, the patient may be any mammal. It may for example be an animal or a human being.

According to the invention, the mode and/or the path of administration of the biocompatible polymer may be as defined above.

According to the invention, the mode and/or the path of administration of the hyaluronic acid may be as defined above, preferably by injection into the biological tissue.

According to the invention, the frequency of administration of the biocompatible polymer may be as defined above.

According to the invention, the frequency of administration of the hyaluronic acid may be as defined above.

In the present document, cosmetic treatment means a non-therapeutic cosmetic treatment.

According to the invention, the non-therapeutic cosmetic treatment may be anti-aging cosmetic treatment, cosmetic treatment for the prevention of cutaneous aging, cosmetic treatment of cutaneous aging, and/or cosmetic treatment of mature skin.

Indeed, as mentioned above, the inventors of the present invention have surprisingly demonstrated that the composition according to the invention makes it possible to stimulate the hydration of the tissues in a synergic manner, advantageously over time and in particular associated with the creation of an improved tissue environment, surprisingly extending the effect of the hyaluronic acid, while reducing the activity of glycanases and stimulating the response of the proximal cells, advantageously and surprisingly allowing for neo-synthesis of the components of the extracellular matrix, said components being of improved quality, while restoring the distribution and the polarity of the matrix.

For this application it is possible, for example, to use the galenic forms described above. The application on the skin can thus be carried out depending on the galenic form used.

It may, for example, be simple application on the skin, or application accompanied by massaging the skin with the composition of the present invention.

It may, for example, be successive application of the composition according to the invention, comprising a first application, for example by cutaneous injection, of the composition according to the invention, followed by topical application of said composition according to the invention.

The application is preferably carried out using a sufficient quantity of the composition, for example in order to ensure treatment of the entire surface of the skin to be treated. It may for example be a conventional application, such as a cream on the skin. It may for example also be an application in order to form a treatment mask.

The application may be for example daily, weekly, and bi-monthly application. It may for example be an application once a day, twice a day, or less often.

The inventor has also surprisingly demonstrated that the composition according to the invention advantageously makes it possible to more effectively fill in lines, while avoiding possible side-effects compared with the known product, for example collagen and/or botulinum toxin injections. Furthermore, the inventor has demonstrated that the composition according to the invention can be used as a filling agent, for example for lines, but also for injection in esthetic treatments and/or as a filler, for example for hydration and inflation, for example in the region of male or female genital and/or sexual organs.

The present invention thus also relates to the use of a composition comprising a biocompatible polymer of formula AaXxYy or AaXxYyZz and hyaluronic acid according to the invention, as a filling agent and/or filler, for example for organs and/or biological tissue.

The present invention thus also relates to the cosmetic use of a composition comprising a biocompatible polymer of formula AaXxYy or AaXxYyZz and hyaluronic acid according to the invention, as a filling agent and/or filler for skin.

The inventor has also surprisingly demonstrated that the composition according to the invention advantageously makes it possible to improve the scarring of biological tissue lesions, in particular by promoting the hydration of the tissue and filling the lesion. In particular, the inventor has surprisingly demonstrated that the composition according to the invention advantageously makes it possible to promote the cutaneous scarring and/or to improve the appearance of cutaneous lesions, for example scars.

The present invention thus also relates to the cosmetic use of a composition comprising a biocompatible polymer of formula AaXxYy or AaXxYyZz and hyaluronic acid according to the invention for improving the appearance of the skin, for example improving the appearance of cutaneous lesions, for example scars.

The present invention thus also relates to the cosmetic use of a composition comprising a biocompatible polymer of formula AaXxYy or AaXxYyZz and hyaluronic acid according to the invention for treatment of cutaneous lesions.

The inventor has also surprisingly demonstrated that the composition according to the invention advantageously makes it possible to improve the scarring of biological tissue lesions, in particular by promoting the hydration of the tissue, preventing the formation of fibrosis, and filling the lesion.

In particular, the inventor has demonstrated that the composition according to the invention advantageously makes it possible to accelerate the speed and the physical quality of the scar tissue, in particular its mechanical properties, its suppleness, and its hydration.

Furthermore, the inventor has demonstrated, in particular in the examples, that the lesions capable of being treated by the composition according to the invention may be any type of tissue lesion whatever the origin, as well as any type of tissue or organ. In particular, in the light of the examples below in which a wide variety of lesions are treated effectively, a person skilled in the art easily understands and can, in the light of this knowledge, extrapolate the other tissue lesions capable of being treated by the present invention.

In the present document, “tissue lesions” means any lesion or damage of any biological tissue of a mammal that is known to a person skilled in the art. This may for example be a lesion of connective tissue, muscle tissue, bone tissue, cartilage tissue, and/or epithelial tissue. It may, for example, be any lesion of any organ or organelle of a mammal known to a person skilled in the art. It may for example be damage to tissue of the digestive tract, tissue of the gastrointestinal tract, of the food and excretion digestive system, of the genital tract, of the reproductive system, of the optical, olfactive or auditory system, of the sensory system, of the circulatory and/or cardiovascular system, of the respiratory system, of the muscular system, of the locomotive system. It may for example be damage to the gastric tissue, a buccal lesion, damage to the cornea, a tympanic lesion, damage to the cochlea, a skin lesion, for example a wound, a chronic wound, for example a diabetic wound, an ulcerous wound, a bedsore, a cutaneous burn, a necrotizing wound, a venous lesion, an ischemic lesion, for example ischemic necrosis, a lesion due to a heart attack, for example a myocardial infarction, bone damage, for example a fracture, a fracture with bone defect, a non-union bone fracture, an osteochondral lesion, cartilage damage, tendinous damage, a surgical lesion, a lesion due to a surgical operation, a lesion due to medical treatment, for example radiotherapy, damage to the nerve tissue, for example a brain lesion, for example a lesion due to removal of a tumor, damage to the bone marrow, damage to nerve fiber, for example of the locomotive and/or sensorial system, a lesion of the respiratory system, for example pulmonary lesions, a lesion of the circulatory system, for example a lesion of the arteries and/or vessels, a lesion of the digestive, hepatic, renal or urinary system.

The present invention also relates to a composition comprising a biocompatible polymer of formula AaXxYy or AaXxYyZz and hyaluronic acid according to the invention for use as a medicament.

The present invention thus also relates to a composition comprising a biocompatible polymer of formula AaXxYy or AaXxYyZz and hyaluronic acid according to the invention for use as a medicament for the prevention and/or the treatment of tissue lesions.

The present invention thus also relates to a composition comprising a biocompatible polymer of formula AaXxYy or AaXxYyZz and hyaluronic acid according to the invention for use as a medicament for the prevention and/or the treatment of tissue lesions selected from ocular lesions, lesions of the vocal chords, joint lesions, discal lesions, tendinous lesions and/or ligament lesions, lesions of the retina, for example retinal detachment, lesions due to Behçet’s disease, surface lesions for example cutaneous wounds, ulcers, for example ulcers of diabetic wounds, of the stomach.

The inventor has also demonstrated that the composition according to the invention advantageously makes it possible, following administration into a joint, to be a facilitator/hydrator of the joints and/or a joint lubricant, advantageously making it possible to prevent and/or treat joint inflammations, to prevent and/or treat arthritis and/or arthrosis.

The present invention thus also relates to a composition comprising a biocompatible polymer of formula AaXxYy or AaXxYyZz and hyaluronic acid according to the invention for use as a medicament for the prevention and/or the treatment of pathologies and/or conditions of the locomotive system.

According to the invention, pathology and/or conditions of the locomotive system means any pathology and/or conditions known to a person skilled in the art that are capable of modifying and/or altering the functioning of the locomotive system. It may for example be a joint pathology, for example a joint inflammation, arthrosis, arthritis. It may for example be a pathology in the region of the tendons or ligaments, for example an inflammation, a stretch, a flattening, a lesion, a rupture, or a tear. It may for example be a pathology in the region of the spinal column and/or intervertebral discs, for example a displacement, flattening, compression or crushing associated with trauma, age, dehydration, etc.;

The inventor has also demonstrated that the composition according to the invention advantageously allows, following administration into the eye, for filling and reinforcement of the subretinal environment, in particular in cases of retinal detachment, and advantageously protection of the retinal microenvironment in dry and wet ARMD advantageously making it possible to prevent and/or treat lesions of the retina, for example retinal detachment, and/or the treatment of age-related macular degeneration, dry age-related macular degeneration, and wet age-related macular degeneration.

The inventor has also surprisingly demonstrated that the composition according to the invention advantageously makes it possible to improve tissue hydration.

Furthermore, the inventor has demonstrated, in particular in the examples, that the composition according to the invention makes it possible to treat and/or improve the hydration of all types of tissues or organs. In particular, in the light of the examples below in which a wide variety of tissues and organs are treated effectively, a person skilled in the art easily understands and can, in the light of this knowledge, extrapolate the tissues and organs capable of being treated by the present invention.

The present invention thus also relates to a composition comprising a biocompatible polymer of formula AaXxYy or AaXxYyZz and hyaluronic acid according to the invention for use as a medicament for the prevention and/or the treatment of tissue dryness.

The present invention thus also relates to a composition comprising a biocompatible polymer of formula AaXxYy or AaXxYyZz and hyaluronic acid according to the invention for use as a medicament for the prevention and/or the treatment of tissue dryness selected in particular from dryness of naturally moist mucous membranes, for example the ocular surface, the buccal, vaginal or nasal mucous membranes, the tissues in contact with biological fluids such as synovial, cephalospinal, peritoneal, pericardiac fluids, bone marrow, joint tissues, epitheliums, for example of the bladder, of the lymphatic system, of the spinal cord.

Furthermore, the inventor has demonstrated, in particular in the examples, that the composition according to the invention makes it possible to treat and/or improve the hydration of tissue or organ mucous. In particular, in the light of the examples below in which a wide variety of tissues and organs are treated effectively, a person skilled in the art easily understands and can, in the light of this knowledge, extrapolate the tissues and organs capable of being treated by the present invention.

The present invention thus also relates to a composition comprising a biocompatible polymer of formula AaXxYy or AaXxYyZz and hyaluronic acid according to the invention for use as a medicament for the prevention and/or the treatment of dryness of mucous membranes, for example the vaginal mucous membrane, the buccal mucous membrane.

The present invention thus also relates to a composition comprising a biocompatible polymer of formula AaXxYy or AaXxYyZz and hyaluronic acid according to the invention for use as a medicament for the prevention and/or the treatment of dryness of the eyes.

The inventor has also surprisingly demonstrated that the composition according to the invention advantageously makes it possible to treat fibroses of biological tissues; in particular the inventor has demonstrated that the composition according to the invention surprisingly makes it possible to reduce fibrosis, in particular to synergically reduce the ratio of the syntheses of collagen 3 and collagen 1 (COL3/COL1), the fibrosis being characterized inter alia by an overexpression of COL 3 with respect to COL1.

The present invention thus also relates to a composition comprising a biocompatible polymer of formula AaXxYy or AaXxYyZz and hyaluronic acid according to the invention for use as a medicament for the prevention and/or the treatment of fibrosis.

Furthermore, the inventor has demonstrated, in particular in the examples, that the fibroses capable of being treated by the composition according to the invention may be any type of fibrosis whatever the origin, as well as any type of tissue or organ. In particular, in the light of the examples below in which a wide variety of fibroses are treated effectively, a person skilled in the art easily understands and can, in the light of this knowledge, extrapolate the other fibroses capable of being treated by the present invention. These may for example be fibroses caused by ischemic lesions, for example muscular and/or cardiac ischemic lesions. They may for example be scar fibroses following ischemia or crushing of the skeletal muscle, infarcted cardiac muscle ischemia, fibroses of tendinous tissues or ligaments, of bone tissues for example a bone callus, fibrosis of the digestive tissues, for example in Chron's disease, post-radiation fibroses, hepatic fibroses, pulmonary fibroses, fibroses due to Peyronie's disease, post-surgical fibroses, for example fibroses leading to organ or tissue adhesions, for example fibrosis following gastrointestinal surgery, tendon, nerve, vessel surgery, natural fibroses, for example occurring during glaucoma, for example fibrosis of the Shlemm canal, for example fibroses occurring during Dupuytren's disease, fibroses resulting from carpal tunnel syndrome and/or other tendinous fibroses.

According to the invention the hyaluronic acid is as defined above.

According to the invention the biocompatible polymer of formula AaXxYy or AaXxYyZz is as defined above.

According to the invention, the pharmaceutical or dermatological composition is as defined above.

According to the invention, the frequency of administration of the biocompatible polymer may be as defined above.

According to the invention, the mode and/or the path of administration of the biocompatible polymer may be as defined above.

The inventor has also surprisingly demonstrated that the composition according to the invention may advantageously be used in the treatment of epidermolysis bullosa. In particular, the inventors have surprisingly and unexpectedly demonstrated that the composition comprising a biocompatible polymer of formula AaXxYy or AaXxYyZz and hyaluronic acid advantageously makes it possible to promote the scarring of ulcers in children suffering from epidermolysis bullosa.

The inventor has also surprisingly and unexpectedly demonstrated that the composition according to the invention advantageously makes it possible to promote the scarring of ulcers and also to reduce the pain associated with these ulcers, in a synergic manner.

The present invention thus also relates to a composition comprising a biocompatible polymer of formula AaXxYy or AaXxYyZz and hyaluronic acid according to the invention for use as a medicament for the prevention and/or the treatment of epidermolysis bullosa.

According to the invention the hyaluronic acid is as defined above.

According to the invention the biocompatible polymer of formula AaXxYy or AaXxYyZz is as defined above.

According to the invention, the pharmaceutical or dermatological composition is as defined above. The composition may advantageously be in a form suitable for spraying, for example using a spray.

According to the invention, the frequency of administration of the biocompatible polymer may be as defined above.

According to the invention, the mode and/or the path of administration of the biocompatible polymer may be as defined above. This may for example be cutaneous application, for example by spraying, for example using an atomizer comprising the composition.

The inventor has also surprisingly demonstrated that the composition according to the invention may advantageously be used in the treatment of periodontal diseases.

The present invention thus also relates to a composition comprising a biocompatible polymer of formula AaXxYy or AaXxYyZz and hyaluronic acid according to the invention for use as a medicament for the prevention and/or the treatment the treatment of periodontal diseases.

In the present document, periodontal diseases means any periodontal disease known to a person skilled in the art. It may for example be gum disease or periodontitis.

The inventor has also surprisingly demonstrated that the composition according to the invention may advantageously be used in the treatment of diseases of the buccal mucous membrane.

The present invention thus also relates to a composition comprising a biocompatible polymer of formula AaXxYy or AaXxYyZz and hyaluronic acid according to the invention for use as a medicament for the prevention and/or the treatment of pathologies of the buccal mucous membrane.

In the present document, pathologies of the buccal mucous membrane means any pathology of the buccal mucous membrane known to a person skilled in the art. It may for example be mouth ulcers, gum disease, mucositis.

The inventor has also surprisingly demonstrated that the composition according to the invention may advantageously be used in the treatment of cutaneous burns of whatever cause whatsoever. These may be for example be heat burns, radiation burns, cutaneous burns due to exposure to UV radiation, cutaneous burns due to exposure to ionizing radiation, for example exposure to X-rays or to gamma rays.

The present invention thus also relates to a composition comprising a biocompatible polymer of formula AaXxYy or AaXxYyZz and hyaluronic acid according to the invention for use as a medicament for the prevention and/or the treatment of cutaneous burns.

According to the invention the hyaluronic acid is as defined above.

According to the invention the biocompatible polymer of formula AaXxYy or AaXxYyZz is as defined above. The biocompatible polymer of formula AaXxYy or AaXxYyZz can advantageously have a molecular weight of between 3000 and 150,000 Daltons.

According to the invention, the pharmaceutical or dermatological composition is as defined above. The composition may advantageously be in a form suitable for spraying, for example using a spray and/or a gel. The composition may advantageously be in a form suitable for spraying, for example a spray or a gel, and does not contain fatty acids.

Advantageously, when the composition is in a form suitable for spraying, for example a spray and/or a gel, and does not contain fatty acids, it advantageously makes it possible to treat burns while avoiding the presence of fatty acid residues, thus preventing any possible undesirable effect.

The inventor has also surprisingly demonstrated that the composition according to the invention may advantageously be used in the treatment of degenerative diseases.

The present invention thus also relates to a composition comprising a biocompatible polymer of formula AaXxYy or AaXxYyZz and hyaluronic acid according to the invention for use as a medicament for the prevention and/or the treatment of degenerative diseases.

In the present document, degenerative diseases means any degenerative disease known to a person skilled in the art. These may for example be sequela, for example associated with a vascular cerebral accident, neurodegenerative diseases, for example Alzheimer's disease, for example Parkinson's disease, degeneration of the retina, degenerative disease associated with tissue degradation, for example joint and/or muscular, myopathies, age-related degenerative disease.

The inventor has advantageously demonstrated that the composition comprising a biocompatible polymer of formula AaXxYy or AaXxYyZz and hyaluronic acid makes it possible to recreate a better cellular microenvironment which favors the functional survival and recovery of the tissues, advantageously allowing for slowing and/or treatment of degenerative diseases.

The present invention also relates to a composition for application as a medicament, said composition comprising a biocompatible polymer of formula AaXxYy or AaXxYyZz and hyaluronic acid.

According to the invention the hyaluronic acid is as defined above. According to the invention the biocompatible polymer of formula AaXxYy or AaXxYyZz is as defined above.

The composition is as defined above.

According to the invention, the frequency of administration of the biocompatible polymer may be as defined above.

According to the invention, the mode and/or the path of administration of the biocompatible polymer may be as defined above.

The present invention also relates to a method for treating a patient, comprising any sequence of the following steps:

i. administration of at least one biocompatible polymer, and ii. administration of hyaluronic acid, in which the administrations are concurrent, successive, or alternating.

The biocompatible polymer is as defined above.

The hyaluronic acid is as defined above.

According to the invention, the patient may be any mammal. It may for example be an animal or a human being.

According to the invention, the mode and/or the path of administration of the biocompatible polymer may be as defined above.

According to the invention, the mode and/or the path of administration of the hyaluronic acid may be as defined above, preferably by injection into the biological tissue.

According to the invention, the frequency of administration of the biocompatible polymer may be as defined above.

According to the invention, the frequency of administration of the hyaluronic acid may be as defined above.

According to the invention, the administration of hyaluronic acid and of biocompatible polymers may be simultaneous, for example in one single mixture or composition, or successive.

According to the invention, in the case of successive administration of hyaluronic acid and biocompatible polymers the posology may be, for example for each administration, an administration of hyaluronic acid followed by an administration of biocompatible polymers. For example, the hyaluronic acid may be administered between 1 minute and 48 hours before the administration of the biocompatible polymers.

In other words, even if, in the present description, reference is made to one composition, it is understood that each of the compounds of the composition can be administered concurrently with the other compounds (for example in a single composition or in two compositions, each of these compositions comprising one or more of the above-mentioned components, it being possible for the mode of administration of each of the compounds or composition(s) to be identical or different), or independently of one another, for example successively, for example independent administration of a biocompatible polymer and independent administration of hyaluronic acid, said administrations being carried out on the same patient, concurrently or successively or in an alternating manner, in a sequence as cited above or a different sequence. These different administrations may be carried out independently of one another or in a linked manner (composition or co-administration), via an identical or different mode of administration (injection, ingestion, topical application, etc.), once or twice per week, for one or more weeks, either successive or otherwise.

The invention thus advantageously provides a general and simple response to a complex technical problem for which there is a real and persistent need in the prior art. It is in particular illustrated in a non-limiting manner in the examples below, from which a person skilled in the art can easily extrapolate for all types of conditions, whatever the origin, as well as for all types of tissues or organs.

In particular, the inventor has demonstrated that the present invention can be generalized to all lesions and/or conditions, in particular due to particular common features of the lesions and/or conditions consisting in an alteration of the extracellular matrix.

The present invention also relates to an ex-vivo graft preparation method comprising impregnation of a graft and/or organ to be grafted with a composition comprising a biocompatible polymer of formula AaXxYy or AaXxYyZz and hyaluronic acid as defined above.

The present invention also relates to the use of a composition comprising a biocompatible polymer of formula AaXxYy or AaXxYyZz and hyaluronic acid as defined above for ex-vivo preparation of a graft and/or organ.

The biocompatible polymer is as defined above.

The hyaluronic acid is as defined above.

According to the invention, the impregnation may be carried out by any method known to a person skilled in the art. It may for example be a case of plunging the organ and/or plunging it into a composition comprising a biocompatible polymer of formula AaXxYy or AaXxYyZz and hyaluronic acid as defined above, either by perfusion of a composition comprising a biocompatible polymer of formula AaXxYy or AaXxYyZz and hyaluronic acid as defined above, or by spraying of a composition comprising biocompatible polymer of formula AaXxYy or AaXxYyZz and hyaluronic acid as defined above.

The present invention also relates to the use of a composition comprising a biocompatible polymer of formula AaXxYy or AaXxYyZz and hyaluronic acid as defined above for in-vitro and/or ex-vivo preparation of an implantable biomaterial.

For example for implantable biomaterials the biocompatible polymer may be added for example by impregnation after preparation of the biomaterial, for example for a tissue or an organ. It may for example also be added during the preparation of the biomaterial from the start, for example the biocompatible polymer of formula AaXxYy or AaXxYyZz and hyaluronic acid as defined below may be added in successive layers, for example in a manner similar to 3D printing.

In the present document, “implantable biomaterials” means any implantable biomaterials that are known to a person skilled in the art and/or are commercially available. It may for example be a compatible implantable material, for example of any type, biodegradable, cross-linked or otherwise, preferably colonizable. They may be implantable biomaterials based on cross-linking of proteins, for example collagens, fibrin, polysaccharides, for example dextran, chitin, hyaluronic acid, alginate, cellulose, and the derivatives thereof, biodegradable and biocompatible copolymers based on glycolic, lactic, malic acid, polymers, which can for example make liquid-gel transitions by means of polymerization that can be controlled by temperature, or by enzymes, or irradiation, or by other methods. It may for example be a polymer based on polycaprolactone, polyurethane, polytetrafluoroethylene silicone, based on inorganic salts, for example calcium phosphates or hydroxyapatites. They may for example be material based on or made of ceramic or metal, for example aluminum, steel, titanium, and/or alloys thereof. Advantageously, when the material is a material based on or made of ceramic or metal, the impregnation makes it possible to cover the outside surface of the material; the impregnation can advantageously be carried out by spraying.

According to the invention, the impregnation composition may have a concentration of from 0.1 μg/mL to 1 mg/mL biocompatible polymer as defined above.

According to the invention, the impregnation composition may have a concentration of from 0.5 $mg \cdot mL^{-1}$ to 20 $mg \cdot mL^{-1}$ hyaluronic acid as defined above.

According to the invention, the duration of the impregnation may be from 5 minutes to 24 hours. Advantageously, the duration of the impregnation may depend on the structure of the graft and/or organ and/or implantable material.

Advantageously, the impregnation furthermore makes it possible to improve the effectiveness of the engraftment. Indeed, the inventor has surprisingly demonstrated that the presence of the polymer and hyaluronic acid in the graft and/or organ preservation solution advantageously allows for a synergic protective and anti-apoptotic effect.

Advantageously, the inventor has surprisingly demonstrated that the composition according to the invention makes it possible to achieve a synergic effect, in particular over time, of the combination of the regenerative and protective properties of biocompatible polymers of the general formula AaXxYy or AaXxYyZz, also referred to as RGTA, and the hydrating and mechanical properties of native or modified hyaluronic acid.

Furthermore, the inventor has demonstrated that the composition according to the invention advantageously makes it possible to prevent and/or treat flaws and/or alternations associated with sequela and stress of any kind (mechanical, oxidative, irradiation, etc.) and with the aging of tissues and organs of any origin, in vitro, ex vivo, and in vivo, in humans and animals.

As shown, the composition according to the invention can be used for prevention, slowing, and improvement of marks associated with the aging of tissues, in particular such as those on the skin, for example prevention, slowing, and improvement of lines, rings, loss of elasticity and suppleness or tension, by the presence of marks, cutaneous dryness, the thickness of the skin, and/or the pigmentation.

As shown, the composition according to the invention can be used for the prevention, slowing and/or treatment of joint pathologies, for example the deterioration of the cartilaginous or synovial tissues.

As shown, the composition according to the invention can be used for the prevention, slowing and/or treatment of the alteration of the quality of the epithelium and/or of the corneal stroma and/or of the vitreous humor.

As shown, the composition according to the invention can be used for the prevention, slowing and/or treatment of the alteration of the quality of the epithelium and/or of the vesical stroma.

As shown, the composition according to the invention can be used for the prevention, slowing and/or treatment of all biological tissues and/or fluids in which hyaluronic acid is naturally present, and/or the production of which by the underlying cells and/or tissues can be altered and/or the quality and/or the stability of the hyaluronic acid can be modified and/or altered.

As shown, the composition according to the invention advantageously and surprisingly allows for synergic recovery of the esthetic and functional quality of the skin as a whole, but also together with other tissues, and results in a rejuvenating effect and functional recovery which each of the products alone did not make it possible to achieve individually, and also an unexpected lasting effect.

In addition to what has been shown, an extension of the effects achieved by a first administration of the composition according to the invention can be further improved for example by iterated contribution, for example topically, on the epithelium/epidermis/mucous membranes.

BRIEF DESCRIPTION OF THE FIGURES

FIG. 1 shows examples of the structure of the biocompatible polymer, for example the structure of the families of compounds OTR412 and OTR413, and OTR415

A person skilled in the art could also identify further advantages upon reading the examples below, illustrated by the accompanying drawings given by way of example.

EXAMPLES

In the examples below, different biocompatible polymers, also referred to as RGTA, have been used. Table 2 below summarizes the different biocompatible polymers used in these examples.

TABLE 2 summaries of the different biocompatible polymers (RGTA) used in these examples

| Biocompatible polymer Name of RGTA | Average molecular weight +/− 15% | Example nos. |
|---|---|---|
| CMDS OTR41201 | 3000 | 1, 2, 6 |
| CMDS OTR41202 | 6000 | 1, 2, 6, 12 |
| CMDS OTR41203 | 10,000 | 1, 6, 8, 10 |
| CMDS OTR41205 | 20,000 | 1 |
| CMDS OTR41210 | 40,000 | 1 |
| CMDS OTR4120 | 80,000 | 1, 2, 3, 5, 7, 8, 9, 11, 12, 13, 14, 15, 16, 17 |
| CMDS OTR4122 | 220,000 | 1, 11 |
| CMDS OTR4125 | 500,000 | 1, 11 |
| CMDSA OTR41301 | 3000 | 1, 6 |
| CMDSA OTR41302 | 6000 | 1, 6, 8, 10 |
| CMDSA OTR41303 | 10,000 | 1, 6 |
| CMDSA OTR41305 | 20,000 | 1 |
| CMDSA OTR41310 | 40,000 | 1 |
| CMDSA OTR4131 | 80,000 | 1, 2, 4, 5, 11, 13, 14, 15, 16, 17 |
| CMDSA OTR4132 | 220,000 | 1, 11 |
| CMDSA OTR4135 | 500,000 | 1, 11 |
| CMDSP OTR415 (F6) | 5000 | 18 |

Example 1

Preparation of the RGTA—Testing the Stability of the Hyaluronic Acid in the Presence of RGTA and Hyaluronidase.

The synthesis of the RGTA is broadly described in the prior art, for example in the patent U.S. Pat. No. 7,396,923 entitled "Method for the sulfonation of compounds comprising free hydroxyl (OH) groups or primary or secondary amines," and also in the bibliographic reference Yasunori I. et al., Biomaterials 2011, 32:769e776) and Petit E. et al., Biomacromolecules. 2004 March-April; 5(2):445-52. [17]:

In the examples below, a plurality of known and described RGTAs have been used, of which OTR4120 describes a number of preclinical and clinical publications (RGTA®-based matrix therapy—A new branch of regenerative medicine in locomotion. Barritault D, Desgranges P, Meddahi-Pellé A, Denoix J M, Saffar J L. Joint Bone Spine. 2017 May; 84(3):283-292. doi: 10.1016/j.jbspin.2016.06.012 [18], RGTA® or ReGeneraTing Agents mimic heparan sulfate in regenerative medicine: from concept to curing patients. Barritault D, Gilbert-Sirieix M, Rice K L, Siñeriz F, Papy-Garcia D, Baudouin C, Desgranges P, Zakine G, Saffar J L, van Neck J. Glycoconj J. 2017 June; 34(3):325-338. doi: 10.1007/s10719-016-9744-5 [14]. The compound OTR4131 is a compound comprising a radical Z which is a fatty acid, specifically acetic acid as described in Frescaline G. et al., Tissue Eng Part A. 2013 July; 19(13-14):1641-53. doi: 10.1089/ten.TEA.2012.0377) [19], Randomized controlled trial demonstrates the benefit of RGTA® based matrix therapy to treat tendinopathies in racing horses. Jacquet-Guibon S, Dupays A G, Coudry V, Crevier-Denoix N, Leroy S, Siñeriz F, Chiappini F, Barritault D, Denoix J M. PLoS One. 2018 Mar. 9; 13(3):e0191796. doi: 10.1371/journal.pone.0191796 [20]. Other compounds also described in the patent documents US06689741, US2014301972A1 in which Z is an amino acid such as phenylalanine (Heparan sulfate proteoglycans mediate internalization and propagation of specific proteopathic seeds. Holmes B B, DeVos S L, Kfoury N, Li M, Jacks R, Yanamandra K, Ouidja M O, Brodsky F M, Marasa J, Bagchi D P, Kotzbauer P T, Miller T M, Papy-Garcia D, Diamond M I. Proc Natl Acad Sci USA. 2013 Aug. 13; 110(33):E3138-47. doi: 10.1073/pnas.1301440110 [21]) or another hydrophobic compound (Structure-activity studies of heparan mimetic polyanions for anti-prion therapies. Ouidja M O, Petit E, Kerros M E, Ikeda Y, Morin C, Carpentier G, Barritault D, Brugère-Picoux J, Deslys J P, Adjou K, Papy-Garcia D. Biochem Biophys Res Commun. 2007 Nov. 9; 363(1):95-100 [22]).

Various RGTAs are listed and described in table 1 together with the features thereof, and table 2 specifies the example numbers in which said compounds have been used.

In the example below, various RGTAs have been tested in order to determine the effect thereof on hyaluronic acid, and in particular the determination of a possible protective effect of hyaluronic acid with respect to hyaluronidase according to the method described in several articles, for example, In Vitro Evaluation of the Sensitivity of a Hyaluronic Acid PEG Cross-Linked to Bovine Testes Hyaluronidase Nicola Zerbinati et al Open Access Maced J Med Sci. 2018 Jan. 25; 6(1):20-24 https://doi.org/10.3889/oamjms.2018 [23], Sall I, Férard G. Comparison of the sensitivity of 11 crosslinked hyaluronic acid gels to bovine testis hyaluronidase. Polym-Degrad Stab. 2007; 92:915-919. https://doi.org/10.1016/j.polymdegradstab.2006.11.020.

In this example, hyaluronidase of type 1-S (EC 3.2.1.35) originated from cattle testicles (sigma Aldrich H3506) and was diluted in a phosphate-buffered saline (PBS) at pH 7.2 in order to obtain a solution at 5000 U/mL.

0.3 mL of a gel of 20 mg/mL streptococcus zooepidemicus hyaluronic acid (sigma Aldrich H39390) was deposited at the base of tubes 5 of mL and 25 μL RGTA was added at different concentrations and then incubated overnight at 37° C.

125 μL of the enzyme solution on the surface of the gel was added, and the tubes were incubated for 2 days (h). The reaction was stopped by adding 0.1 mL of solution of potassium tetraborate 0.8 mol/L pH 9.1 followed by agitation in a vortex, followed by heating for 3 minutes at 100° C.

The measurement of the activity of the enzyme by salting out of N-acetyl-D-glucosamine (NAG) was carried out by the Reissig et al method (Reissig J L, Strominger J L, Leloir L F. A modified colorimetric method for the estimation of N-acetylamino sugars. J Biol Chem 1955; 217:959e96 [25].

A solution of Ehrlich's reagent (Sigma Aldrich), diluted 1/10 in acetic acid, is briefly added to each tube (3 mL) which, following vortex agitation in the vortex, are then incubated at 37° for 20 minutes, and then the tubes are centrifugated at 1000 g for 15 minutes, and the supernatant is measured at 585 nm against PBS+Ehrlich's reagent.

Table 3 below summarizes the results obtained for an unmodified constant quantity of hyaluronic acid (300 μL to 20 mg/mL) (molecular weight of 250,000 Daltons in the presence of 125 μL hyaluronidase and an increasing dose of compound of two families of RGTA of different molecular sizes extending from 3000 D to 500,000 D described in table 1.

TABLE 3 results of the degradation of hyaluronic acid in the presence of biocompatible polymers and hyaluronidase

| Non-modified HA | RGTA: 25 μL (μg/mL) RGTA | RGTA OTR 4120 | 41201 | 41202 | 41203 | 41205 | 41210 | 4122 | 4125 |
|---|---|---|---|---|---|---|---|---|---|
| | | % degradation of HA by hyaluronidase +/_ 5% | | | | | | | |
| 300 μL of | 50 | 5% | 4% | 5% | 5% | 5% | 5% | 5% | 5% |
| HA gel at | 10 | 5% | 9% | 6% | 6% | 5% | 5% | 5% | 5% |
| 20 mg/mL | 1 | 40% | 45% | 46% | 48% | 44% | 40% | 40% | 40% |
| | 0 | 100% | 100% | 100% | 100% | 100% | 100% | 100% | 100% |
| RGTA | | 4131 | 41301 | 41302 | 41303 | 41305 | 41310 | 43132 | 4135 |
| 300 μL of | 50 | 3% | 5% | 5% | 5% | 5% | 5% | 5% | 5% |
| HA gel at | 10 | 4% | 8% | 7% | 6% | 5% | 5% | 5% | 5% |
| 20 mg/mL | 1 | 38% | 45% | 44% | 44% | 42% | 40% | 40% | 40% |
| | 0 | 100% | 100% | 100% | 100% | 100% | 100% | 100% | 100% |

Legend of table 3: 300 μL of gel + 25 μL RGTA + 100 μL (800 U) enzyme incubated for 2 days at 37° C. Stopped by 0.1 mL potassium tetraborate (0.8 mol/L, pH 9.1) Vigorous vortex mixing, heating for 3 min at 100° C., and addition of 3 mL of Ehrlich's reagent and reading at 585 nM.

As shown in table 3 above, the RGTAs have an inhibiting effect on the activity of the hyaluronidase and/or a protective effect on the hyaluronic acid. This example also clearly shows that the effect is dose-dependent. The dose at 25 μL of RGTA at 10 μg/mL is just as effective as that at 50 μg/mL. This example also clearly and advantageously shows that a low concentration (1 μg/mL biocompatible polymer (RGTA) advantageously allows for an inhibition of over 60% of the degradation of the hyaluronic acid by the hyaluronidase. This example also shows that there is no significant difference in the protective effect for RGTA against degradation by the hyaluronidase according to the molecular weight of the RGTAs, or between the carboxymethyl dextran sulfate RGTA, specifically OTR41201, OTR41202, OTR41203, CMDS OTR41205, CMDS OTR41210, CMDS OTR4120, CMDS OTR4122, CMDS OTR4125, or acetylated carboxymethyl dextran sulfate RGTA, specifically OTR41301, CMDSA OTR41302, CMDSA OTR41303, CMDSA OTR41305, CMDSA OTR41310, CMDSA OTR4131, CMDSA OTR4132, CMDSA OTR4135 described in table 1 above.

Example 2

Synergic Effect of the RGTA and the HA on the Synthesis of the Collagens, on the Reduction of the Fibrotic Index, and on the Polarity of the Collagen Secretion The RGTAs are also known to modulate the expression of the collagens and the fibrosis (US06689741, US2014301972A1 [4]) in the skin, from a number of articles describing said properties, in particular in the treatment of cutaneous fibrosis (Garcia-Filipe et al.2007 [8]), the muscular tissues (A substituted dextran enhances muscle fiber survival and regeneration in ischemic and denervated rat EDL muscle. Desgranges P, Barbaud C, Caruelle J P, Barritault D, Gautron J. FASEB J. 1999 April; 13(6):761-6 [26]), cardiac tissues (New agents for the treatment of infarcted myocardium. Yamauchi H, Desgranges P, Lecerf L, Papy-Garcia D, Tournaire M C, Moczar M, Loisance D, Barritault D. FASEB J. 2000 November; 14(14):2133-4), bone tissues (Barritault et al 2017 [18]) or digestive tissues (Alexakis et al, 2004 [5]). However, the effect of a possible combination of RGTA with HA has not been studied and is not known.

Human dermal fibroblasts were placed in a culture in 24-hole well plates according to the protocols described according to Garcia-Filipe S et al 2007 [8].

The fibroblasts sown at 10,000 cells per well are cultivated for 5 days in order to achieve the confluence with 90,000 cells per well, then placed in a serum-free medium for 24 hours in the presence of 15 mCi/mL of 5-3 H proline and 50 mg/mL ascorbic acid in the presence or absence of RGTA OTR4120 or OTR4131 at 10 and 100 μg/mL and HA (20 mg/mL) according to the protocol below.

The culture medium and the cells are harvested separately after 24 hours, dialyzed against water, digested by pepsin, and the phenotypes of collagens are analyzed following separation by electrophorese in SDS gel according to the method described in Asselot-Chapel C, et al Expression of fibronectin and interstitial collagen genes in smooth muscle cells: modulation by low molecular weight heparin fragments and serum. Biochem Pharmacol. 1995 Mar. 1; 49(5): 653-9 [28].

The zones corresponding to collagens 1 and 3 have been cut out of the gel, and the tritium is counted. The % of the total cellular collagen is the ratio between the radioactivity in the cellular layer and the radioactivity in the supernatant.

Table 4 below summarizes the results obtained.

| RGTA | RGTA 100 μg/mL | HA 20 mg/mL | COL3: dpm $^{3}H$/ 1000 cells (+/−10%) | COL1 dpm $^{3}H$/ 1000 cells (+/−10%) | COL3/ COL1* | Total % cellular COL |
|---|---|---|---|---|---|---|
| | − | − | 170 | 720 | 0.23 | 7 |
| | − | + | 170 | 960 | 0.177 | 7 |
| heparin | | + | 100 | 600 | 0.166 | 15 |
| CMDS OTR4120 | + | − | 60 | 720 | 0.083 | 30 |
| CMDS OTR4120 | + | + | 60 | 1100 | 0.054 | 45 |
| CMDS OTR41201 | + | − | 45 | 720 | 0.062 | 8 |
| CMDS OTR41201 | + | + | 45 | 1100 | 0.041 | 35 |
| CMDS OTR41202 | + | − | 45 | 720 | 0.062 | 6 |
| CMDS OTR41202 | + | + | 45 | 1100 | 0.041 | 35 |
| CMDSA OTR4131 | + | − | 60 | 730 | 0.082 | 30 |
| CMDSA OTR4131 | + | + | 60 | 1180 | 0.050 | 45 |

*A measurement in normal mouse skin, using comparable techniques, gives a COL1 to COL3 ratio of 10 (FIG. 1 of Garcia-Filipe S et al, 2007 [8]).

As shown in table 4 above, the RGTAs have an effect on the regulation and the synthesis of collagens, by reducing the quantity of collagen 3 by almost 3 times (from 170 to 60, which results, in vivo, in a reduction of the fibrosis), as well as the effect of the HA on a 20% increase (720 vs 960) of the synthesis of collagen 1.

As shown in table 4 below, the combination of polymer and hyaluronic acid unexpectedly has a synergic effect for the synthesis of COL1, with an increase of 40% (720 to 1100).

As shown in table 4 below, the combination of polymer and hyaluronic acid furthermore unexpectedly has a synergic effect on the polarization of the collagen secretion in the region of the cells and the matrix thereof. The % of collagen goes from 7% to 45%, i.e. 6.4 times more, with respect to all the total collagen accumulated in the cellular and pericellular space.

As shown in this example, the composition comprising a polymer of formula AaXxYy or AaXxYyZz and hyaluronic acid advantageously allows, in a synergic manner, for an increase in the collagen synthesis, an improvement in the collagen synthesis, and advantageously makes it possible to recreate the matrix space which favors good cellular and tissue differentiation.

Example 3

Synergic Effect of RGTA and HA in Ex-Vivo Use on Tympanic, Corneal and Biomaterial Membranes, and in 3D Printing Methods for Tissues or Organs 3-1. Pre-Incubation of Tympanic and Corneal Membranes Before Organ Transplantation/Preservation In this example, OTR4120 was used at 10 μ/mL in a solution of 5 mg/mL commercial HA (of injectable quality), originating in particular from different providers, in order to impregnate the graft, for example the cornea or the ear drum, for a few minutes. The impregnation is carried out before the graft is performed, and then at the end of the operation some drops of the same solution are added.

In the view of the surgeons, the engagement and functional recovery were of much better quality than that observed according to the protocols of the prior art.

3-2. Pre-Incubation of Biomaterials for Bone or Cartilage Filling with the Product of the Invention.

In this example a plurality of bone substitute biomaterials used for bone, cartilage or intervertebral disc reconstruction were impregnated with a solution comprising the combination according to the invention, i.e. a combination of polymer of formula AaXxYy or AaXxYyZz and HA, before being implanted.

In this example, the impregnation solution used comprises OTR4120 at a concentration of 10 μg/mL, and a hyaluronic acid concentration of 1 mg/mL.

The impregnated biomaterials being decellularized bone powders, or synthesis products such as ceramics, in particular tricalcium phosphate or TCP, or hydroxyapatite HA, or composite biomaterials further comprising proteins such as collagen.

3-3. Use of a Composition Comprising a Combination of Polymer of Formula AaXxYy or AaXxYyZz and Hyaluronic Acid (HA) as Ink in 3D Printing Methods for Tissues or Organs In this example, the composition used comprises 10 at a concentration of 100 μg/mL, and a hyaluronic acid concentration of 1 to 20 mg/mL according to the printing methods or processes described in various reviews, in particular Jammed Microgel Inks for 3D Printing Applications. Highley C B, Song K H, Daly A C, Burdick J A. Adv Sci (Weinh). 2018 Oct. 24; 6(1):1801076. doi: 10.1002/advs.201801076. [33], Collagen/heparin sulfate scaffolds fabricated by a 3D bioprinter improved mechanical properties and neurological function after spinal cord injury in rats. Chen C, Zhao M L, Zhang R K, Lu G, Zhao C Y, Fu F, Sun H T, Zhang S, Tu Y, Li X H. J Biomed Mater Res A. 2017 May; 105(5):1324-1332. doi: 10.1002/jbm.a.36011. [34] Development and Evaluation of Hyaluronic Acid-Based Hybrid Bio-Ink for Tissue Regeneration. Lee J, Lee S H, Kim B S, Cho Y S, Park Y. Tissue Eng Regen Med. 2018 Sep. 21; 15(6):761-769. doi: 10.1007/s13770-018-0144-8. [35]

As shown in the example above, it is clear that the composition comprising a polymer of formula AaXxYy or AaXxYyZz and hyaluronic acid makes it possible to achieve synergic effects, in particular in vitro, which advantageously make it possible to recreate the matrix space which favors good cellular and tissue differentiation. Furthermore, this example clearly shows that this effect can be achieved for all the applications and or tissue requiring the production and/or recreation and/or increase of the extracellular matrix.

This example also clearly shows, in particular by way of the stimulation of the production of components of the extracellular matrix, that the composition comprising a polymer of formula AaXxYy or AaXxYyZz and hyaluronic acid furthermore advantageously makes it possible to protect the hyaluronic acid from degradation, and moreover to extend the effects of the HA in its uses for tissue filling and hydration.

It is also clearly apparent that the composition comprising a polymer of formula AaXxYy or AaXxYyZz and hyaluronic acid allows for an improvement of the organization and the distribution and the polarization of the production of the matrix components, such as the collagens, advantageously making it possible to improve the quality of the extracellular matrix and generally of the treated tissue, whatever the tissues or organs in question.

It is also clearly apparent that, in the case of a lesion or microlesion of a biological tissue, the composition comprising a polymer of formula AaXxYy or AaXxYyZz and hyaluronic acid allows for a substitution both of the heparan sulfates and of the hyaluronic acid destroyed during the lesion, by the polymer of formula AaXxYy or AaXxYyZz, and the hyaluronic acid, respectively, present in the composition according to the invention.

Furthermore, during the injection of the composition according to the invention, possible destruction of the matrix space may take place, at the actual site of penetration of the composition and then extend by diffusion of the injected composition, causing microlesions associated with the infilling of the filling space. These microlesions may lead to a local inflammation reaction and destruction of the microenvironment and the matrix architecture. The polymer of formula AaXxYy or AaXxYyZz can thus take the place of endogenic heparan sulfates, the destruction of which may be activated in response to this tissue aggression by the inflammatory tissue response, and can thus assist in the reconstruction of the matrix architecture while the hyaluronic acid fills the space of the microenvironment. The glycanases caused by the lesion may be activated, but are advantageously inhibited by the polymer of formula AaXxYy or AaXxYyZz, furthermore advantageously allowing for a reduction and allowing for an extended period of tissue filling. Moreover, as shown, the composition comprising a polymer of formula AaXxYy or AaXxYyZz and hyaluronic acid having a synergic and unexpected effect on the fibroblastic dermal cells advantageously makes it possible to increase the synthesis and the quantity of collagen 1 (COL1), and reinforcement of the tissue matrix, whatever the tissues.

This example therefore clearly demonstrates that the composition comprising a polymer of formula AaXxYy or AaXxYyZz and hyaluronic acid advantageously makes it possible to reinforce the barrier function of the skin, allows for an improvement on the quality and the appearance of the skin, in particular by improving the hydration, thickness, suppleness, etc. thereof. Furthermore, this example also clearly demonstrates that the effect is lasting, in particular due to the inhibition of enzymes responsible for the degradation of the collagen, but also due to the induction/stimulation of the collagen synthesis.

Moreover, this example also clearly demonstrates that the composition comprising a polymer of formula AaXxYy or AaXxYyZz and hyaluronic acid advantageously makes it possible to recreate an extracellular matrix of better quality, which in turn will indirectly cause a better-quality cellular response. This looped effect will extend the beneficial duration of the treatment and the anti-aging effect.

Example 4

Use of a Composition Comprising a Biocompatible Polymer of Formula AaXxYy or AaXxYyZz and Hyaluronic Acid for Treatment of Cutaneous Aging In this example, cosmetic compositions comprising RGTA OTR4131 and hyaluronic acid were used by topical application. In particular, a day cream referred to as FOR075.039 containing 1 μg/mL RGTA OTR4131 with 20 mg/mL hyaluronic acid (molecular weight—400 to 700 kD), a night cream referred to as FOR075.040 containing 1 μg/mL RGTA OTR4131 with 20 mg/mL hyaluronic acid (molecular weight—400 to 700 kD) and a serum referred to as FOR075.041 containing 2 μg/mL RGTA OTR4131 with 40 mg/mL hyaluronic acid (molecular weight—400 to 700 kD) were used. Hyaluronic acid originating from Biphil. (http://www.biophilgroup.com/).

Tables 5 to 7 summarize the characteristics of the compositions used; the biocompatible polymer of formula AaXxYyZz used is designated sodium carboxymethyl dextran acetate sulfate in these tables:

TABLE 5 day cream formulation

| INCI EU designation | % (m/m) in the product |
|---|---|
| Aqua | 66.6899 |
| Caprylic/Capric triglyceride | 8.5000 |
| Glycerin | 8.5000 |
| Pentylene glycol | 5.0000 |
| Coco-caprylate | 3.4984 |
| Coconut alkanes | 2.8000 |
| Hydroxyethyl acrylate/sodium acryloyldimethyl taurate copolymer | 1.7000 |
| Acrylates copolymer | 1.4100 |
| Coco caprylate/caprate | 0.7000 |
| Parfum | 0.5000 |
| Ethylhexylglycerin | 0.3000 |
| Sodium hyaluronate | 0.2000 |
| Sorbitan isostearate | 0.1100 |
| VP/polycarbamyl polyglycol ester | 0.0500 |
| Hydrolyzed sesame protein pg-propyl methylsilanediol | 0.0400 |
| Tocopherol | 0.0016 |
| Sodium carboxymethyl dextran acetate sulfate | 0.0001 |

TABLE 6 night cream formulation

| INCI EU designation | % (m/m) in the product |
|---|---|
| Aqua | 53.4999 |
| Helianthus annuus seed oil | 10.0000 |

TABLE 6-continued

| night cream formulation | |
|---|---|
| INCI EU designation | % (m/m) in the product |
| Octyldodecyl myristate | 8.0000 |
| Coconut alkanes | 6.4000 |
| Glycerin | 5.0000 |
| Pentylene glycol | 5.0000 |
| Glyceryl stearate citrate | 4.0000 |
| Zea mays starch | 2.5000 |
| Glyceryl stearate | 2.0000 |
| Coco caprylate/caprate | 1.6000 |
| Tocopheryl acetate | 1.0000 |
| Ethylhexylglycerin | 0.3000 |
| Xanthan gum | 0.3000 |
| Parfum | 0.2000 |
| Sodium hyaluronate | 0.2000 |
| Sodium carboxymethyl dextran acetate sulfate | 0.0001 |

TABLE 7

| serum formulation | |
|---|---|
| INCI EU designation | % (m/m) in the product |
| Aqua | 82.1598 |
| Glycerin | 6.4000 |
| Pentylene glycol | 5.0000 |

TABLE 7-continued

| serum formulation | |
|---|---|
| INCI EU designation | % (m/m) in the product |
| Caprylic/Capric triglyceride | 2.0000 |
| Helianthus annuus seed oil | 2.0000 |
| Sodium acrylates copolymer | 0.7000 |
| Polyglyceryl-3 methylglucose distearate | 0.5000 |
| Sodium hyaluronate | 0.4000 |
| Lecithin | 0.3000 |
| Ethylhexylglycerin | 0.3000 |
| Parfum | 0.2000 |
| Terminalia ferdinandiana fruit extract | 0.0400 |
| Sodium carboxymethyl dextran acetate sulfate | 0.0002 |

This study was carried out on a target population of women of an average age of 62±1 year (of 47 and 67 years of age) and whose skin type and phototype are distributed as follows:

50% had a combination skin, 9% normal, and 43% dry, divided into two phototypes: 59% type 2 and 41% type 3.

The application and the application frequency are described in table 8 below. The results were analyzed using the 3D Primo system (trade mark) Lite, the Conomètre (trade mark), DUB (trade mark), Skin Scanner Conomètre (trade mark), and clinical scores of questionnaires, collection of possible

TABLE 8

| application and use protocol for the compositions | | | |
|---|---|---|---|
| | Zones | Frequency | Mode |
| Day - FOR075.039 | At home: face and neckline; In the laboratory: treated zone defined in the region of the legs (relates to 11 volunteers only). | At home: once per day (morning) before putting on makeup, after washing and applying the serum. In the laboratory: a single standard application (2 µl/cm$^2$) in synergy with two other products. | At home: apply in the region of the face by lightly massaging until it has penetrated completely. In the laboratory: massage lightly and uniformly using a finger-stall. |
| Night - FOR075.040 | | At home: once a day (evening) after washing. In the laboratory: a single standard application (2 µl/cm$^2$) in synergy with two other products. | |
| Serum - FOR075.041 | | At home: once a day (morning) after washing and before the day cream. In the laboratory: a single standard application (2 µl/cm$^2$) in synergy with two other products. | At home: apply in the region of the face by lightly massaging until it has penetrated completely, focusing on the zone of the lines and the zone having blemishes. In the laboratory: massage lightly and uniformly with a finger-stall. |

In this example, the following effects of the compositions were studied:

anti-aging effect;
smoothing effect;
detoxifying effect;
effect on the cutaneous firmness, elasticity, and suppleness;
redensifying/replumping effect;
hydrating effect.

In particular, the following parameters were evaluated:

the smoothing/anti-wrinkle effect of the products studied by measurements using the 3D Primos® system Lite;
their detoxifying effect by clinical scoring carried out by the technician in charge of the study;
their effect on the biomechanical properties of the skin by measurements using the Cutomètre®;
their redensifying effect, by means of density measurements of the dermis using the DUB® Skin Scanner;
their hydrating effect two and four hours after single standard application in the laboratory by means of measurements using the Cornéomètre® (relates to only 11 volunteers);
taking and collecting replica skin impressions in polymeric silicone Silflo®
subjectively assessing their cosmetic acceptability, their effectiveness and their subsequent use by analyzing the volunteers' responses to a subjective evaluation questionnaire.
collecting possible undesirable reactions.

The results obtained are summarized in the following tables 9 to 13:

TABLE 9

| results following application of the composition | | | | | | | |
|---|---|---|---|---|---|---|---|
| Parameters | Kinetics | Δ (average ± standard deviation) | Variations between the kinetics (average ± TMS) | Type of statistical analysis | p | Significance | % of volunteers presenting |
| Radiance and | ΔJ7 | 23% | 0.9 ± 0.1 | Wilcoxon | <0.0001 | Yes | 86% |
| brightness of the skin | ΔJ28 | 42% | 1.6 ± 0.1 | Wilcoxon | <0.0001 | Yes | 100% |
| Uniformity of | ΔJ7 | 5% | 0.2 ± 0.1 | NA | NA | NA | 27% |
| the complexion | ΔJ28 | 34% | 1.2 ± 0.2 | Wilcoxon | <0.0001 | Yes | 86% |
| Texture of | ΔJ7 | 10% | 0.4 ± 0.1 | NA | NA | NA | 32% |
| the skin | ΔJ28 | 38% | 1.3 ± 0.2 | Wilcoxon | <0.0001 | Yes | 86% |
| Coolness of | ΔJ7 | 27% | 1.0 ± 0.1 | Wilcoxon | <0.0001 | Yes | 91% |
| the skin | ΔJ28 | 47% | 1.7 ± 0.2 | Wilcoxon | <0.0001 | Yes | 95% |

TABLE 10

| Variation in the parameters of cutaneous relief compared with the initial state | | | | | | | |
|---|---|---|---|---|---|---|---|
| | | Δ (average ± standard | Δ % over the | Statistical analysis | | | % of volunteers presenting the |
| | Kinetics | deviation) | average | P | Significant | Test | anticipated effect |
| Average roughness: Ra (in μm) | Δ J28 | −0.5 ± 0.2 | −3% | 0.034 | Yes | Test t | 68% |
| Average relief: Rz (in μm) | Δ J28 | −2.2 ± 1.0 | −3% | 0.041 | Yes | Test t | 68% |

TABLE 11

| Variation in the biomechanical properties of the skin after 28 days of daily use (compared with the initial state) | | | | | | | |
|---|---|---|---|---|---|---|---|
| | | | COMPARISON BEFORE/AFTER ON THE ZONE TREATED BY THREE | | | | |
| | | | ΔJX-J0 in mm (average ± standard | Student test t | | % | % of volunteers presenting the |
| | | Kinetics | deviation | p | Significance | effectiveness | anticipated effect |
| FIRMNESS | Parameter R0 (i.e. Uf) | Δ J28 | −0.021 ± 0.012 | 0.088 | Yes | 6% | 45% |
| RAW ELASTICITY | Parameter R7 (i.e. Ur/Uf) | Δ J28 | 0.116 ± 0.015 | <0.001 | Yes | 47% | 91% |
| TONE | Parameter Ur (i.e. R7*R0) | Δ J28 | 0.035 ± 0.006 | <0.001 | Yes | 39% | 73% |

TABLE 12

| Variation in the rate of cutaneous hydration following single standard application of the products in synergy (compared with a non-treated zone) | | | | | | |
|---|---|---|---|---|---|---|
| | | Δ Δ Tx-T0 | Statistics | | % | % of volunteers presenting an |
| Parameter | Kinetics | (average ± TMS) | p= | Significance | effectiveness | improvement |
| Rate of cutaneous hydration | Δ t2h | 17 ± 1 | <0.001 | Yes | 80% | 100% |
| | Δ t4h | 20 ± 1 | <0.001 | Yes | 90% | 100% |

TABLE 13

| summary of the results obtained | |
|---|---|
| Parameters | Results |
| Cutaneous hydration | T2H: Average improvement of 80% in 100% of users.<br>T4H: Average improvement of 90% in 100% of users. |
| Anti-wrinkle | J28: Average 3% reduction in relief and roughness of the skin in 68% of users. |
| Radiance and brightness | J7: Average improvement of 23% in 86% of users.<br>J28: Average improvement of 42% in 100% of users. |
| Uniformity of complexion | J28: Average improvement of 34% in 86% of users. |
| Texture of the skin | J28: Average improvement of 38% in 86% of users. |
| Coolness of the skin | J7: Average improvement of 27% in 91% of users.<br>J28: Average improvement of 47% in 95% of patients. |
| Elasticity | J28: Average improvement of 47% in 91% of patients. |
| Tone | J28: Average improvement of 39% in 73% of users. |

As shown in the tables above, the examples of compositions according to the invention have advantageously made it possible to increase the cutaneous hydration, having an anti-wrinkle effect, to improve the radiance and brightness of the skin, the uniformity of the complexion, the texture of the skin, the coolness of the skin, the elasticity, and the tone of the skin.

Table 14 below contains the results obtained, and demonstrates the effectiveness of the composition used.

| Properties | Favorable |
|---|---|
| General assessment | |
| Pleasant to use | 100% |
| Pleasant appearance | 100% |
| Rapid penetration | 100% |
| Pleasant scent | 91% |
| Leaves skin non-greasy | 100% |
| Leaves skin non-greasy and non-sticky | 96% |
| Effectiveness perceived by the user | |
| Leaves the skin soft | 100% |
| Makes the skin supple | 100% |
| Makes the skin hydrated and nourished | 100% |
| Regenerates the skin | 96% |
| Smooths lines and wrinkles | 95% |
| Has a firming effect | 96% |
| Revives the brightness of the complexion | 95% |
| Improves the texture of the skin | 96% |
| Those around me think I look younger | 86% |

No undesirable reaction was observed during the study, and the compositions were popular with the majority of the volunteers for its characteristics and its effectiveness. Indeed, over 95% of the subjects wished to continue use of the tested compositions.

As shown in above, the examples of compositions according to the invention have advantageously made it possible to increase the cutaneous hydration in a synergic manner, having an anti-wrinkle effect, to improve the radiance and brightness of the skin, the uniformity of the complexion, the texture of the skin, the coolness of the skin, the elasticity and the tone of the skin.

Furthermore, this example clearly demonstrates that the examples of the composition according to the invention comprising a polymer of formula AaXxYy or AaXxYyZz and hyaluronic acid advantageously make it possible to improve the appearance of the skin, as a cutaneous anti-aging effect, in particular an anti-wrinkle effect, and makes it possible to smooth the skin. Furthermore, this example clearly demonstrates that the examples of the composition according to the invention comprising a polymer of formula AaXxYy or AaXxYyZz and hyaluronic acid advantageously make it possible to detoxify the skin, while increasing and improving the mechanical properties thereof, for example its elasticity and its suppleness.

Furthermore, this example clearly demonstrates that the examples of the composition according to the invention comprising a polymer of formula AaXxYy or AaXxYyZz and hyaluronic acid advantageously make it possible to improve the hydration of the skin.

Example 5

Effect on Filling in Lines by Intradermal or Subcutaneous Injection of the RGTA and HA Mixture Use of RGTA 4120 or OTR 4131 via subcutaneous injection and injection of HA in order to reduce lines, and over the duration of this effect, was performed by doctors and/or patients.

The administrations were carried out at the sole initiative of doctors or patients, for themselves and by themselves (it being possible for the patient to be a doctor), or by myself on myself, using commercially available sterile products based on OTR4120 or OTR4131, and HA which is also available (depending on the country from the Internet or otherwise), sometimes from samples originally intended for research.

In all cases, these uses were off-label, the two products RGTA and HA of different sources were administered in different indicated combinations and according to different indicated modes of operation, and the effects are summarized below.

A plurality of different formulations and operating modes were implemented, sometimes by the patients themselves, in various line regions (in particular crow's feet, forehead lines, frown lines, lines around the mouth, nasolabial folds, labiodental folds, bags under the eyes, neck lines, etc.

The administration modes were, independently, as follows:

- co-injection of a mixture of hyaluronic acid HA and RGTA OTR4120 or 4131 was performed in the syringe prior to injection (being able to be repeated in 1 month), or
- injection of HA followed by injection, after 24 hours or 48 hours, of the mixture of RGTA (OTR4120 or 4131) and HA.

The RGTA OTR 4120 or OTR 4131 being in sterile solution in physiological serum, respectively at 100 μg/mL (in vials of 5 mL) and at 10 μg/mL (in vials of 1 mL).

The injected volumes of RGTA alone do not exceed 1 mL per injection site.

The mode of injection being performed using needles of the insulin or mesotherapy type.

Hyaluronic acid or HA is of different natural origins of different sizes or cross-linked, and freely commercially available, depending on the country (via websites, or at a pharmacy, or via distribution networks with doctors).

The HA is in solution between 0.5 and 25 mg/mL, preferably between 10 and 20 mg/mL.

The effect on lines is evaluated by the satisfaction of the individual treated.

In all cases an improvement is identified from two weeks, with a visible effect and disappearance of signs of inflammation (redness, pain) associated with the injection process. This rapid effect is also a surprising effect, in particular the rapid disappearance of signs of inflammation.

After 1 month, but also after 6 months, the effects are confirmed and there is a high level of satisfaction for all the treatments. This effect over time is unusual; the duration is observed even in the case of natural HA that is not cross-linked and is of a high molecular weight.

This example therefore clearly demonstrates that an example of the composition according to the invention comprising a polymer of formula AaXxYy or AaXxYyZz and hyaluronic acid advantageously makes it possible to improve the appearance of the skin and may be used for filling in lines and/or wrinkles. Furthermore, this example clearly demonstrates that an example of the composition according to the invention comprising a polymer of formula AaXxYy or AaXxYyZz and hyaluronic acid advantageously makes it possible to achieve a rapid effect, without undesirable side-effects, while limiting a possible inflammatory reaction.

This example clearly demonstrates that an example of the composition according to the invention comprising a polymer of formula AaXxYy or AaXxYyZz and hyaluronic acid advantageously makes it possible to improve the appearance of the skin and may be used for filling in lines and/or wrinkles without requiring multiple and/or repeated applications of the composition.

Finally, this example clearly demonstrates that an example of the composition according to the invention comprising a polymer of formula AaXxYy or AaXxYyZz and hyaluronic acid advantageously makes it possible to improve the appearance of the skin and may be used for filling in lines and/or wrinkles in a lasting manner, for example for 6 months following application.

Example 6

Use of Polymers of Formula AaXxYy or AaXxYyZz and Hyaluronic Acid Against Cutaneous Aging In this example, compositions for topical application are prepared. This is a topical formulation comprising OTR41201 or OTR41202 or OTR41203 or indeed the family of OTR413101, OTR413102, OTR413103 at doses of 0.1 1, 10 or 100 μg/mL of the final product, in particular compositions for topical application are prepared, comprising OTR41201 or OTR41202 at doses of from 1 to 10 μg/mL with or without hyaluronic acid at concentrations of from 0.1 mg/mL, preferably 20 mg/mL, preferably 10 mg/mL.

The cream formulations correspond to those used in example 4.

These compositions are used as an application alone, but also in addition to application and/or treatment for filling in lines using a composition comprising a polymer of formula AaXxYy or AaXxYyZz and hyaluronic acid, as described in example 5 above.

In this example, following filling in of lines as described in example 5 above, the above-mentioned topical composition comprising OTR41201 or OTR412002 at doses of 0.1, 1, 10 or 100 μg/mL of the final product, in particular compositions for topical application are prepared, comprising OTR41201 or OTR412002 at doses of from 1 to 10 μg/mL with or without hyaluronic acid at concentrations of from 0.1 mg/mL, preferably 20 mg/mL, is applied to the zone which has been treated previously.

The polymer of formula AaXxYy or AaXxYyZz used, specifically OTR41201 or OTR41202, advantageously has a low molecular weight which advantageously makes it possible to pass through the barrier of the epidermis and can penetrate into the zone of the dermis and reinforces the local effect of the composition previously administered. For example it can advantageously further increase the secretion of collagens and their polarity, but also increase the production of HA against degradation by glycanase, and maintain and/or further extend the favorable effect of the RGTA and HA on the cellular microenvironment.

Furthermore, this example clearly demonstrates that the examples of the composition according to the invention comprising a polymer of formula AaXxYy or AaXxYyZz and hyaluronic acid advantageously make it possible to improve the appearance of the skin, advantageously makes it possible to improve the structure of the skin, in particular due to an increase in the secretion of collagens and the polarity thereof, but also to increase the protection of the HA against degradation by glycanases. Furthermore, this example clearly demonstrates that the examples of the composition according to the invention comprising a polymer of formula AaXxYy or AaXxYyZz and hyaluronic acid advantageously make it possible to achieve a lasting effect over time, and/or advantageously makes it possible to further extend the favorable synergic effect of the polymers of formula AaXxYy or AaXxYyZz and hyaluronic acid on the cellular microenvironment.

Example 7

Use of Polymers of Formula AaXxYy or AaXxYyZz and Hyaluronic Acid in Treating Vaginal Dryness via Injection In this example, the composition used is the composition described in example 5 above, comprising 10 μg/mL OTR4120 and 20mg/mL HA from different sources, in physiological serum. The mixture is prepared by taking 100 μL of a solution of OTR4120 by means of a syringe, then, after having connected said syringe, via an adapter, to the syringe containing the HA solution to be injected, passing the contents from one syringe to the other.

In one case, small injections, i.e. 100 μl of composition, very superficial, of the product of the invention were carried out in the mucous membranes of the region located between the vagina and the opening of the labia minora. They are distributed over a dozen sites around the circumference of the vagina, just behind the opening. The injection zones were then massaged afterward, in order to uniformly spread out the product. A comparison of the filling and/or hydrating effect on the tissue is carried out between the composition comprising a polymer of formula AaXxYy or AaXxYyZz and hyaluronic acid, compared with a usual composition comprising just hyaluronic acid. According to the doctor, the effect achieved using an example of a composition according to the invention, i.e. comprising a polymer of formula AaXxYy or AaXxYyZz and hyaluronic acid, was considered to be better, over time, than treatment using a composition comprising just hyaluronic acid.

This example clearly demonstrates that the examples of the composition according to the invention comprising a polymer of formula AaXxYy or AaXxYyZz and hyaluronic acid advantageously make it possible to treat and/or improve vaginal dryness. In particular, this example clearly demonstrates that the examples of the composition according to the invention make it possible to hydrate biological tissues, in particular mucous membranes, in particular the vaginal mucous membrane.

Example 8

Use of Polymers of Formula AaXxYy or AaXxYyZz and Hyaluronic Acid for Treating Vaginal Dryness In this example, the composition used is the composition described in example 7 above, i.e. a composition containing 10 μg/mL OTR4120 and 20 mg/mL HA from different sources, in physiological serum. The gel is applied to a finger, and the vaginal mucous membranes are massaged. This treatment can be carried out a few weeks after injection performed according to example 7.

The use of a gel prepared using OTR41203 has also been reported to be very effective.

This example clearly demonstrates that the examples of the composition according to the invention comprising a polymer of formula AaXxYy or AaXxYyZz and hyaluronic acid advantageously make it possible to treat and/or improve vaginal dryness. In particular, this example clearly demonstrates that the examples of the composition according to the invention, in particular in topical application, make it possible to hydrate biological tissues, in particular mucous membranes, in particular the vaginal mucous membrane.

Example 9

Use of Polymers of Formula AaXxYy or AaXxYyZz and Hyaluronic Acid for Treating Dry Eyes In this example, the composition used corresponds to an eyewash comprising hyaluronic acid including CACICOL (trade mark) based on RGTA OTR4120 at 100 μg/mL. Thus, 3 to 4 dosettes of CACICOL, i.e. approximately 1.3 mL OTR4120 at 100 μg/mL or 1 mL CACIPLIQ (OTR4120 at 100 μg/mL) are added to 10 mL of a 0.15 g/mL solution of hyaluronic acid (for example in a multi-dose vial of the type ABAK thealose (Thea laboratories) or Viskyal or Aqualarm.

Several patients suffering from severe eye dryness (Sjogren) were treated with the eyewash mixture comprising hyaluronic acid and a polymer of formula AaXxYy or AaXxYyZz, specifically OTR4120, by administration of one drop every 6 hours. The need to add the drop of the mixture at this frequency fades away very rapidly, to reach 2 and then 1 drop per day and to stabilize at one drop every two or three days. A reduction in eye dryness was observed in particular by way of a reduction in the patient's need to apply the product and/or the reduction in the frequency of the treatment and of the duration of the treatment, in particular compared with the usual eyewash. This effect is described for the eyewash CACICOL (Evaluation of a new matrix regenerating agent in patients with Sjögren syndrome and superficial ulcerative keratitis resistant to conventional therapy: A report of 3 cases. Fajnkuchen F, Barritault D, Giocanti-Aurégan A. Medicine (Baltimore). 2018 March; 97(10):e9935. doi: 10.1097/MD.0000000000009935. [29]). However, and surprisingly, the effect is much quicker in the case of the combination according to the invention, i.e. a polymer of formula AaXxYy or AaXxYyZz and hyaluronic acid, and is moreover more stable, in particular advantageously making it possible to promote the reconstruction of a longer lasting lachrymal system, in particular maintaining application of the composition according to the invention.

This example clearly demonstrates that the examples of the composition according to the invention comprising a polymer of formula AaXxYy or AaXxYyZz and hyaluronic acid advantageously make it possible to treat and/or improve eye dryness. In particular, this example clearly demonstrates that the examples of the composition according to the invention, in particular in topical application, make it possible to hydrate biological tissues, in particular the cornea, and advantageously makes it possible to promote and/or restore the lachrymal system.

Example 10

Use of Polymers of Formula AaXxYy or AaXxYyZz and Hyaluronic Acid for Rehydration, Preservation of Dryness, and Hair Regrowth In this example, the product used is made up of laluset cream (Genevrier laboratory (www.laboratoires-genevrier-.com)) containing a mixture of 0.2% hyaluronic acid in 100 g mixed with 1 mg OTR41302 in physiological serum. This cream is used every 3 days and massaged into the hair.

This treatment exhibits an effect of preventing hair loss, advantageously being able to stimulate hair regrowth in the subjects treated, while compositions containing only HA alone or RGTA alone have not exhibited effects, in particular any notable effects.

The composition described in example 8 above can also be used for this application.

This example clearly demonstrates that the examples of the composition according to the invention comprising a polymer of formula AaXxYy or AaXxYyZz and hyaluronic acid advantageously make it possible to rehydrate the scalp, while hydrating the capillary fiber. Furthermore, this example clearly demonstrates that the examples of the composition according to the invention comprising a polymer of formula AaXxYy or AaXxYyZz and hyaluronic acid advantageously make it possible to prevent hair loss and/or to stimulate hair regrowth. Furthermore, this example clearly demonstrates that the examples of the composition according to the invention comprising a polymer of formula AaXxYy or AaXxYyZz and hyaluronic acid advantageously make it possible to prevent and/or treat alopecia.

Example 11

Use of Polymers of Formula AaXxYy or AaXxYyZz and Hyaluronic Acid for the Treatment of Superficial Skin Burns (Heat or Post-Radiation) or Lesions Caused by Peeling and Skin Ulcers Resulting from Detachment of the Epidermis, or Lesions of the Skin or Mucous Membranes, for Example After an Episiotomy In this example, the compounds used are identical to those described in example 6 or that described in example 10 above.

Compositions are prepared in a spray form, comprising from 0.05 to 1% hyaluronic acid and 10 μg/mL OTR4132 or OTR4135 or OTR4120 or OTR4122 or OTR4125 in physiological serum (or water). These compositions have been found to be particularly appropriate and effective for treating surface burns. Furthermore, the use of the formulation, in particular in the form of a spray, has made it possible to prevent pain and the risk of aggravation of the lesion which may occur during application of the composition.

Said aqueous solution formula for a spray advantageously does not contain fatty acid, which avoids the risk of causing by the presence of residues of fatty acids that are not yet eliminated and originate from cream are the cause of aggravation of the burn by a "barbecue" effect.

This formulation has also exhibited a degree of effectiveness, in a synergic manner, in bringing about better quality scarring and in reducing pain, which it was not possible to observe in any of the products used separately.

The products based on RGTA and having very high molecular weights, in particular OTR4122, OTR4125 and the forms containing acetylated groups of OTR4132 and OTR4135, dispensed as a spray and in a mixture with hyaluronic acid, have proven to be even more effective, in particular when said spray has been used on patients suffering from epidermolysis bullosa, further improving the effects described in the case of this pathology with OTR4120 alone (A Rapid Response to Matrix Therapy With RGTA in Severe Epidermolysis Bullosa. Malaq A A, Barritault D. Eplasty. 2012; 12:ic15 [30]). Furthermore, the use of the combination and/or composition according to the invention advantageously makes it possible to obtain closed wounds which are more solid and/or the scarring of which is more effective, for example closed wounds which appear more resistant to re-opening.

Likewise, the pain has been remarkably reduced during topical application of the product in spray form or in gel form, as described in the example for epidermolysis bullosa, or during scarring of an episiotomy by topical application of the gel (according to example 8) or of the spray.

Furthermore, these examples clearly demonstrate that the examples of the composition according to the invention comprising a polymer of formula AaXxYy or AaXxYyZz and hyaluronic acid advantageously make it possible to promote scarring, for example of wounds and/or cutaneous burns. Furthermore, this example clearly demonstrates that the examples of the composition according to the invention comprising a polymer of formula AaXxYy or AaXxYyZz and hyaluronic acid advantageously make it possible to promote the scarring of cutaneous ulcers originating from epidermolysis bullosa, or lesions due to incision or tearing of mucous membranes, and furthermore advantageously allows for lasting scarring having an increased scar quality and a reduction of the pain.

Example 12

Use of Polymers of Formula AaXxYy or AaXxYyZz and Hyaluronic Acid for Treating Mouth Ulcers, Gum Disease or Mucositis In this example, aqueous formulations comprising RGTA OTR4120 or RGTA OTR41202 at 10 μg/mL mixed with hyaluronic acid (10 mg/mL) are prepared. The aqueous solutions are arranged independently in glass vials of 20 mL, closed by a stopper provided with a pump delivering 140 μL/at each touch. The composition is sprayed directly into the mouth of patients suffering from mouth ulcers, gum disease, or mucositis. Thus, the products of the invention, in particular administered in the form of a spray, exhibit a greatly improved level of effectiveness for the treatment of mouth ulcers, gum disease and mucositis, and in particular the effect on the treatment of mouth ulcers, gum disease and mucositis is much faster than each of the products taken separately.

This example clearly demonstrates that the examples of the composition according to the invention comprising a polymer of formula AaXxYy or AaXxYyZz and hyaluronic acid advantageously make it possible to treat mouth wounds and/or pathologies. In particular, this example clearly demonstrates that the examples of the composition according to the invention comprising a polymer of formula AaXxYy or AaXxYyZz and hyaluronic acid advantageously make it possible to treat mouth ulcers, gum disease and mucositis, and to thus promote the repair and/or to improve the appearance and/or the structure of buccal mucous membranes.

Example 13

Use of Polymers of Formula AaXxYy or AaXxYyZz and Hyaluronic Acid in Treating Changes to the Locomotive System (Joints, Tendons, Ligaments, Intervertebral Discs) and Mandibular Joints In this example, the formulations used combine RGTA OTR4120 or OTR4131 at 10 μg/mL with hyaluronic acid typically used at preferred concentrations of from 10 to 25 mg/mL, such as those used in example 5.

The composition is applied by injection close to the injured region or directly on the site of the lesion, for example via the intra-articular path if the lesion is chondral, osteoarticular, or intra-tendinous, or peri-tendinous, or intramuscular in the case of tearing or straining. The products of the invention diffuse easily in and around the region of the lesion, filling the space created by the lesion.

The persons treated independently exhibit a pathology and/or change of the locomotive system, for example in the region of the joints, i.e. such as in arthritis of the knee or hip, and temporary jaw troubles, in the region of tendons, i.e. partial tears of the tendinous or ligamental fibers as already described by Jacquet-Guibon S, 2018 [20] with OTR4131 products in sport horses, or in the review by Barritault D et al. [18], in particular in the fusion of vertebrae [18] or injection close to the region of the intradiscal zone, or in the thesis by Carnicer David, Preliminary report—ultrasonographic evolution of tendon lesions treated with RGTA in horses, Maison Alfort National Veterinary School, February 2009 [36], in the region of the ligaments in an example of mandibular joint difficulties treated by injection into the zone in the periarticular region close to the fibrocartilaginous articular disc, discal ligaments, and manducatory muscles, or indeed in the region of the intervertebral discs, specifically in the zone of flattening of an intervertebral disc (L1).

In these treatments, the result and effect are rapid, in particular an immediate disappearance of the pain, and furthermore advantageously the effect is long-lasting, over more than a year, in particular associated with topical application of an example of a composition according to the invention, in particular of the cream described in example 6 advantageously comprising polymers of a low molecular weight, for example from 3000 to 6000 Daltons, associated or not with HAs.

The results obtained and the effects using an example of a composition according to the invention are advantageously greater than those obtained using RGTA alone, as described in the study Jacquet-Guibon S, 2018 [20] or Carnicer [36].

Furthermore, a particularly beneficial, surprising, and unexpected effect has advantageously been observed for an injectable preparation for treatments of joint and tendinous damage. The same applies for a case of pain associated with damage to intervertebral discs, the pain having disappeared without reappearing after more than a year.

This example clearly demonstrates that the examples of the composition according to the invention comprising a polymer of formula AaXxYy or AaXxYyZz and hyaluronic acid advantageously make it possible to treat pathologies and/or conditions of the locomotive system. In particular, this example clearly demonstrates that the examples of the composition according to the invention comprising a polymer of formula AaXxYy or AaXxYyZz and hyaluronic acid advantageously make it possible to treat joint damage, tendinous damage, pathologies associated with the intervertebral disc, for example compression of the disc, damage to the disc, for example by restoring the structure thereof and/or by promoting the scarring thereof. Furthermore, this example also clearly demonstrates that the examples of the composition according to the invention comprising a polymer of formula AaXxYy or AaXxYyZz and hyaluronic acid advantageously make it possible to treat pain in a synergic manner, for example pain associated with damage to intervertebral discs.

Example 14

Use of Polymers of Formula AaXxYy or AaXxYyZz and Hyaluronic Acid in Treating Periodontal Diseases In this example, the composition used in independently that described in examples 5 or 13. The composition is used independently in particular in local application in the region of the damage, by filling, injection of periodontal pockets, bone grafts.

The composition is either injected directly into the gums or into the region of the periodontal pocket, or deposited in said pocket.

Following application, the composition according to the invention has allowed for an improved resorption of periodontal damage or engraftment as observed using the products based on the polymer of formula AaXxYy or AaXxYyZz used alone. Furthermore, an example of a composition according to the invention has advantageously made possible treatment of periodontal pathologies, in particular filling in a lack of tooth-supporting tissues, and restoration of gums.

Furthermore, the results obtained by means of an example of a composition according to the invention exhibit improved effectiveness and, unexpectedly, a synergic effect in treatment compared with results obtained using RGTA alone, for example as described in Barritault D et al. 2017 [18] or, in the view of a person skilled in the art, compared with results obtained using HA alone.

Example 15

Dental Paste Comprising Polymers of Formula AaXxYy or AaXxYyZz and Hyaluronic Acid The composition according to the invention comprising a biocompatible polymer and hyaluronic acid can easily be incorporated into all types of dental pastes, and used for topical application as toothpaste.

In this example, the dental pastes are pastes, in particular for twice-daily use, independently comprising a concentration of RGTA OTR4120 or OTR4131 of 1 μg/mL and a concentration of hyaluronic acid of 20 mg/mL.

The dental paste is useful in particular for twice-daily use and advantageously allows for treatment and/or prevention of periodontal diseases.

Example 16

Use of Polymers of Formula AaXxYy or AaXxYyZz and Hyaluronic Acid in Treating Fibrosis, Example of Tissue Adhesions In this example, compositions comprising a concentration of RGTA OTR4120 or OTR4131 of 10 μg/mL and a concentration of hyaluronic acid of from 5 to 20 mg/mL are used.

As demonstrated in example 2, RGTAOTR4120 or OTR4131 at 10 μg/mL combined with hyaluronic acid has a synergic effect not only for reducing the quantity of collagen 3 which is over-expressed in fibrosis, but also for increasing that of collagen 1 so as to achieve a COL3/COL1 ratio which is very close to that of a normal tissue, but also by its capacity to promote the secretion of the basal and not the apical side.

This property of the mixture is in particular exploited in the case of a use of the product of the invention in the form of a spray, for example as described in examples 6, 10 and 12, for a post-surgical open application. For example following laparotomy and covering the tissues and organs by atomization of the spray prior to closure, or at the moment of introducing an implant, for example a pacemaker, prostheses, catheters, for which it is desirable to reduce the adhesion of the connective tissue which takes place over time.

In these indications, the use of the spray has been found to be very effective and has been able to be verified in particular in a patient for whom a second laparotomy was performed.

This example clearly demonstrates that the examples of the composition according to the invention comprising a polymer of formula AaXxYy or AaXxYyZz and hyaluronic acid advantageously make it possible to prevent and/or treat fibroses. In particular, this example clearly demonstrates that the examples of the composition according to the invention comprising a polymer of formula AaXxYy or AaXxYyZz and hyaluronic acid advantageously make it possible to prevent the formation of an adhesion plate, for example in the abdominal region, for example following abdominal surgery.

Example 17

Use of Polymers of Formula AaXxYy or AaXxYyZz and Hyaluronic Acid in Treating Fibrosis In this example, compositions comprising a concentration of RGTA OTR4120 or OTR4131 of 10 μg/mL and a concentration of hyaluronic acid of from 0.1 to 2 mg/mL are used.

In this example, the fibroses are fibroses which are present in particular in the region of the muscle or brain ischemia.

The administration of the compositions is carried out according to the usual methods known to a person skilled in the art.

The RGTA is known for protective and antifibrotic effects on the functional recovery of muscle [26; 27] or brain ischemia (Theranostics. 2018 Nov. 12; 8(21):5814-5827. doi: 10.7150/thno.28252. eCollection 2018., A heparan sulfate-based matrix therapy reduces brain damage and enhances functional recovery following stroke. Khelif Y, Toutain J, Quittet M S, Chantepie S, Laffray X, Valable S, Divoux D, Sineriz F, Pascolo-Rebouillat E, Papy-Garcia D, Barritault D, Touzani O, Bernaudin M. [31]).

In this example, the combination of RGTA, for example OTR4120 or 4131, with hyaluronic acid will also have a synergic effect in the treatment of fibrosis, and in addition in the functional recovery of the fibrotic muscle treated.

This example clearly demonstrates that the examples of the composition according to the invention comprising a polymer of formula AaXxYy or AaXxYyZz and hyaluronic acid can advantageously make it possible to treat fibroses, in particular muscular fibroses. In particular, this example clearly demonstrates that the examples of the composition according to the invention comprising a polymer of formula AaXxYy or AaXxYyZz and hyaluronic acid can advantageously make it possible to prevent the formation of fibrosis, while improving the functional recovery of the tissue, for example of the fibrotic muscle.

Example 18

Use of Polymers of Formula AaXxYy or AaXxYyZz and Hyaluronic Acid in Treating Degenerative Diseases In this example, compositions comprising a concentration of RGTA OTR4120 or OTR4131 of 10 μg/mL and a concentration of hyaluronic acid of from 0.1 to 2 mg/mL are used.

The RGTA is also known for its effects in treating neurodegenerative diseases (EP 12305414 [32]), in particular by intra-arterial or intra-cerebral administration of RGTA.

The administration of the compositions is carried out according to the usual methods known to a person skilled in the art, in particular by intra-arterial or intra-cerebral administration.

The subjects suffer in particular from neurodegenerative diseases, for example as described in EP 12305414 [32].

In this example, the combination of RGTA, for example OTR4120 or 4131, with hyaluronic acid will also have a synergic effect in the treatment of neurodegenerative diseases.

LIST OF REFERENCES

1. Modified hyaluronic acid based materials for biomedical applications. Tiwari S, Bahadur P. Int J Biol Macromol. 2019 January; 121:556-571. doi:10.1016/j.ijbiomac.2018.10.049. Epub 2018 Oct. 12. Review.
2. Hyaluronic acid, a promising skin rejuvenating biomedicine: A review of recent updates and pre-clinical and clinical investigations on cosmetic and nutricosmetic effects. Bukhari S N A, Roswandi N L, Waqas M, Habib H, Hussain F, Khan S, Sohail M, Ramli N A, Thu H E, Hussain Z. Int J Biol Macromol. 2018 December; 120(Pt B): 1682-1695. doi:10.1016/j.ijbiomac.2018.09.188. doi:10.1016/j.ijbiomac.2018.09.188
3. Reduction of postoperative adhesion development. Diamond M P. Fertil Steril. 2016 October; 106(5):994-997.e1. doi:10.1016/j.fertnstert.2016.08.029. Epub 2016 Sep. 10. Review.
4. Patent document US06689741, US2014301972A1
5. Reversal of abnormal collagen production in Crohn's disease intestinal biopsies treated with regenerating agents. Alexakis C, Caruelle J P, Sezeur A, Cosnes J, Gendre J P, Mosnier H, Beaugerie L, Gallot D, Malafosse M, Barritault D, Kern P. Gut. 2004 January; 53(1):85-90.
6. Insights on a new path of pre-mitochondrial apoptosis regulation by a glycosaminoglycan mimetic. Yue X L, Lehri S, Li P, Barbier-Chassefière V, Petit E, Huang Q F, Albanese P, Barritault D, Caruelle J P, Papy-Garcia D, Morin C. Cell Death Differ. 2009 May; 16(5):770-81. doi: 10.1038/cdd.2009.9
7. Differential effect triggered by a heparan mimetic of the RGTA family preventing oral mucositis without tumor protection. Mangoni M, Yue X, Morin C, Violot D, Frascogna V, Tao Y, Opolon P, Castaing M, Auperin A, Biti G, Barritault D, Vozenin-Brotons M C, Deutsch E, Bourhis J. Int J Radiat Oncol Biol Phys.2009 Jul. 15; 74(4):1242-50. doi:10.1016/j.ijrobp.2009.03.006
8. RGTA OTR4120, a heparan sulfate mimetic, is a possible long-term active agent to heal burned skin. Garcia-Filipe S, Barbier-Chassefiere V, Alexakis C, Huet E, Ledoux D, Kerros M E, Petit E, Barritault D, Caruelle J P, Kern P J Biomed Mater Res A. 2007 January; 80(1):75-8
9. Patent document EP1677807
10. Heparin-like synthetic polymers, named RGTAs, mimic biological effects of heparin in vitro. Rouet V, Meddahi-Pellé A, Miao H Q, Vlodaysky I, Caruelle J P, Barritault D. J Biomed Mater Res A.2006 Sep. 15; 78(4):792-7
11. FGF protection and inhibition of human neutrophil elastase by carboxymethyl benzylamide sulfonate dextran derivatives. Meddahi A, Lemdjabar H, Caruelle J P, Barritault D, Hornebeck W. Int J Biol Macromol. 1996 February; 18(1-2):141-5.
12. Human plasmin enzymatic activity is inhibited by chemically modified dextrans. Ledoux D, Papy-Garcia D, Escartin Q, Sagot M A, Cao Y, Barritault D, Courtois J, Hornebeck W, Caruelle J P. J Biol Chem. 2000 Sep. 22; 275(38):29383-90

13. Heparan sulfate mimetics modulate calpain activity during rat Soleus muscle regeneration. Zimowska M, Szczepankowska D, Streminska W, Papy D, Tournaire M C, Gautron J, Barritault D, Moraczewski J, Martelly I. J Cell Physiol. 2001 August; 188(2):178-87.
14. RGTA® or ReGeneraTing Agents mimic heparan sulfate in regenerative medicine: from concept to curing patients. Barritault D, Gilbert-Sirieix M, Rice K L, Siñeriz F, Papy-Garcia D, Baudouin C, Desgranges P, Zakine G, Saffar J L, van Neck J. Glycoconj J.2017 June; 34(3):325-338. doi:10.1007/s10719-016-9744-5
15. Tammi R., Agren U M., Tuhkanen A L., Tammi M. Hyaluronan metabolism in skin. Progress in Histochemistry & Cytochemistry. 29(2):1-81, 1994
16. R. Stern et al., European Journal of Cell Biology 58 (2006) 699-715)
17. Yasunori I. et al., Biomaterials 2011, 32:769e776) et Petit E. et al., Biomacromolecules. 2004 March-April; 5(2):445-52.
18. RGTA®-based matrix therapy—A new branch of regenerative medicine in locomotion. Barritault D, Desgranges P, Meddahi-Pellé A, Denoix J M, Saffar J L. Joint Bone Spine. 2017 May; 84(3):283-292. doi: 10.1016/j.jbspin.2016.06.012.
19. Frescaline G. et al., Tissue Eng Part A. 2013 July; 19(13-14):1641-53. doi:10.1089/ten.TEA.2012.0377).
20. Randomized controlled trial demonstrates the benefit of RGTA® based matrix therapy to treat tendinopathies in racing horses. Jacquet-Guibon S, Dupays A G, Coudry V, Crevier-Denoix N, Leroy S, Siñeriz F, Chiappini F, Barritault D, Denoix J M. PLoS One. 2018 Mar. 9; 13(3):e0191796. doi:10.1371/journal-.pone.0191796
21. Heparan sulfate proteoglycans mediate internalization and propagation of specific proteopathic seeds. Holmes B B, DeVos S L, Kfoury N, Li M, Jacks R, Yanamandra K, Ouidja M O, Brodsky F M, Marasa J, Bagchi D P, Kotzbauer P T, Miller T M, Papy Garcia D, Diamond M I. Proc Natl Acad Sci USA. 2013 Aug. 13; 110(33): E3138-47. doi: 10.1073/pnas.1301440110
22. Structure-activity studies of heparan mimetic polyanions for anti-prion therapies. Ouidja M O, Petit E, Kerros M E, Ikeda Y, Morin C, Carpentier G, Barritault D, Brugère-Picoux J, Deslys J P, Adjou K, Papy-Garcia D. Biochem Biophys Res Commun. 2007 Nov. 9; 363(1):95-100.
23. In Vitro Evaluation of the Sensitivity of a Hyaluronic Acid PEG Cross-Linked to Bovine Testes Hyaluronidase Nicola Zerbinati et al Open Access Maced J Med Sci. 2018 Jan. 25; 6(1):20-24 https://doi.org/10.3889/oamjms.2018
24. Sall I, Férard G. Comparison of the sensitivity of 11 crosslinked hyaluronic acid gels to bovine testis hyaluronidase. PolymDegrad Stab. 2007; 92:915-919. https://doi.org/10.1016/j.polymdegrad-stab.2006.11.020.
25. Reissig J L, Strominger J L, Leloir L F. A modified colorimetric method for the estimation of N-acetylamino sugars. J Biol Chem 1955; 217:959e96.
26. A substituted dextran enhances muscle fiber survival and regeneration in ischemic and denervated rat EDL muscle. Desgranges P, Barbaud C, Caruelle J P, Barritault D, Gautron J. FASEB J. 1999 April; 13(6):761-6.
27. New agents for the treatment of infarcted myocardium. Yamauchi H, Desgranges P, Lecerf L, Papy-Garcia D, Tournaire M C, Moczar M, Loisance D, Barritault D. FASEB J. 2000 November; 14(14):2133-4.
28. Asselot-Chapel C, et al Expression of fibronectin and interstitial collagen genes in smooth muscle cells: modulation by low molecular weight heparin fragments and serum. Biochem Pharmacol. 1995 Mar. 1; 49(5): 653-9.
29. Evaluation of a new matrix regenerating agent in patients with Sjögren syndrome and superficial ulcerative keratitis resistant to conventional therapy: A report of 3 cases. Fajnkuchen F, Barritault D, Giocanti-Auregan A. Medicine (Baltimore). 2018 March; 97(10):e9935. doi: 10.1097/MD.0000000000009935.
30. A Rapid Response to Matrix Therapy With RGTA in Severe Epidermolysis Bullosa. Malaq A A, Barritault D. Eplasty. 2012; 12:ic15.
31. Theranostics. 2018 Nov. 12; 8(21):5814-5827. doi: 10.7150/thno.28252. eCollection 2018., A heparan sulfate-based matrix therapy reduces brain damage and enhances functional recovery following stroke. Khelif Y, Toutain J, Quittet M S, Chantepie S, Laffray X, Valable S, Divoux D, Sineriz F, Pascolo-Rebouillat E, Papy-Garcia D, Barritault D, Touzani O, Bernaudin M.
32. EP 12305414
33. Jammed Microgel Inks for 3D Printing Applications., Highley C B, Song K H, Daly A C, Burdick J A. Adv Sci (Weinh). 2018 Oct. 24; 6(1):1801076. doi:10.1002/advs.201801076.
34. Collagen/heparin sulfate scaffolds fabricated by a 3D bioprinter improved mechanical properties and neurological function after spinal cord injury in rats. Chen C, Zhao M L, Zhang R K, Lu G, Zhao C Y, Fu F, Sun H T, Zhang S, Tu Y, Li X H. J Biomed Mater Res A. 2017 May; 105(5):1324-1332. doi:10.1002/jbm.a.36011. Epub 2017
35. Development and Evaluation of Hyaluronic Acid-Based Hybrid Bio-Ink for Tissue Regeneration. Lee J, Lee S H, Kim B S, Cho Y S, Park Y. Tissue Eng Regen Med. 2018 Sep. 21; 15(6):761-769. doi: 10.1007/s13770-018-0144-8. eCollection 2018 December.
36. Carnicer David, Preliminary report—ultrasonographic evolution of tendon lesions treated with RGTA in horses, Maison Alfort National Veterinary School, February 2009

The invention claimed is:

1. A method for non-therapeutic or therapeutic treatment of an individual, comprising administering a composition consisting of:

a biocompatible polymer of the general formula (II) below $$AaXxYyZz \quad (II)$$

in which:

A represents a monomer,

X is —$CH_2$—COO— or carboxymethyl, Y is —$SO_3$ or —$SO_3Na^+$, and Z is —$OCCH_3$ or phenylalanine, a represents the number of monomers, x represents the rate of substitution of the monomers A by the groups X, y represents the rate of substitution of the monomers A by the groups Y, hyaluronic acid, and a pharmaceutical, dermatological or cosmetic support to the individual, wherein the method is for the treatment of fibrosis, tissue dryness, mucous membrane dryness, cosmetic treatment of skin aging, cosmetic treatment of cutaneous aging, cosmetic treatment of mature skin, and/or treatment of lesions of the respiratory system, and wherein the monomer is glucose, wherein the number of monomer "a" is such that the mass of said polymers of formula (II) greater than or equal to 3000 Daltons, wherein the rate of substitution "x" is between 10 and 150%, wherein the rate of substitution "y" is between 10 and 170%, and wherein the rate of substitution "z" of all the monomers A, by the groups Z, is between 1 and 50%.

2. The method of claim 1, wherein Z is —$OCCH_3$.

3. The method of claim 1, wherein Z is phenylalanine.

4. The method of claim 1, wherein the method is for the treatment of tissue dryness.

5. The method of claim 1, wherein the method is for the treatment of fibrosis.

6. The method of claim 1, wherein the method is for the treatment of cosmetic treatment of skin aging.

7. The method of claim 1, wherein the method is for the treatment of mucous membrane dryness.

8. The method of claim 1, wherein the method is for treatment is for cosmetic treatment of cutaneous aging.

9. The method of claim 1, wherein X is —$CH_2$—COO—, Y is —$SO_3$, and Z is —$OCCH_3$.

10. The method of claim 1, wherein X is —$CH^2$—COO—, Y is —$SO^3$, and Z is-phenylalanine.

11. The method of claim 1, wherein the support is a dermatological or cosmetic support.

12. The method of claim 1, wherein the method is for the treatment of cosmetic treatment of mature skin.

13. The method of claim 1, wherein the method is for the treatment of and/or lesions of the respiratory system.

* * * * *